US010245423B2

(12) United States Patent
Jung et al.

(10) Patent No.: US 10,245,423 B2
(45) Date of Patent: Apr. 2, 2019

(54) METHOD FOR MANUFACTURING MICROSTRUCTURE USING CENTRIFUGAL FORCE AND MICROSTRUCTURE MANUFACTURED BY SAME

(71) Applicant: JUVIC INC., Seoul (KR)

(72) Inventors: Hyung Il Jung, Seoul (KR); Hui Suk Yang, Seoul (KR); Su Yong Kim, Seoul (KR)

(73) Assignee: JUVIC INC., Seoul ( * ) Notice: Subject to any disclaimer, the term of this patent is extended or adjusted under 35 U.S.C. 154(b) by 381 days.

(21) Appl. No.: 14/889,808

(22) PCT Filed: May 2, 2014

(86) PCT No.: PCT/KR2014/003964
§ 371 (c)(1),
(2) Date: Nov. 6, 2015

(87) PCT Pub. No.: WO2014/182022
PCT Pub. Date: Nov. 13, 2014

(65) Prior Publication Data
US 2016/0067469 A1    Mar. 10, 2016

(30) Foreign Application Priority Data

May 6, 2013 (KR) .................. 10-2013-0050462
May 2, 2014 (KR) .................. 10-2014-0053423

(51) Int. Cl.
*A61M 37/00* (2006.01)
*B29C 41/08* (2006.01)
(Continued)

(52) U.S. Cl.
CPC ....... *A61M 37/0015* (2013.01); *B29C 41/085* (2013.01); *C09D 101/08* (2013.01);
(Continued)

(58) Field of Classification Search
None
See application file for complete search history.

(56) References Cited

U.S. PATENT DOCUMENTS 5,286,181 A * 2/1994 Schwager ............ A23G 3/0247
264/13
2002/0138049 A1 9/2002 Allen et al.
(Continued)

FOREIGN PATENT DOCUMENTS

EP         1183064 B1    12/2012
JP      2005154321 A     6/2005
(Continued)

OTHER PUBLICATIONS

Lin et al., "Silicon-Processed Microneedles", Journal of Microelectromechanical Systems, 1999, vol. 8, No. 1, pp. 78-84.
(Continued)

*Primary Examiner* — Monica A Huson
*Assistant Examiner* — Kelsey C Grace
(74) *Attorney, Agent, or Firm* — Knobbe Martens Olson & Bear LLP

(57) ABSTRACT

The present invention relates to a method for manufacturing a microstructure, the method comprising the steps of: (a) preparing a viscous composition on a lower substrate; and (b) applying centrifugal force to the viscous composition to induce extension of the viscous composition, thereby manufacturing a microstructure. According to the present invention, (i) a microstructure having a micro-unit diameter and sufficient effective length and hardness is provided; (ii) any process that may destroy activation of a drug or cosmetic component, such as high-temperature treatment, organic solvent treatment, etc., is avoided; (iii) loss resulting from contact and separation is reduced; (iv) the limitation of aspect ratio of the manufactured microstructure is overcome; (v) the limitation of yield resulting from flatness is over-
(Continued)

come; and (vi) microstructures of various shapes can be manufactured.

13 Claims, 32 Drawing Sheets

(51) Int. Cl.
C09D 101/08 (2006.01)
A61K 9/50 (2006.01)
B29L 31/00 (2006.01)

(52) U.S. Cl.
CPC .... *A61K 9/5089* (2013.01); *A61M 2037/0046* (2013.01); *A61M 2037/0053* (2013.01); *B29K 2995/0056* (2013.01); *B29L 2031/7544* (2013.01)

(56) References Cited

U.S. PATENT DOCUMENTS

| 2007/0276330 | A1* | 11/2007 | Beck | A61M 37/0015 604/172 |
| 2010/0030100 | A1* | 2/2010 | Tokumoto | A61B 10/0035 600/556 |
| 2010/0114043 | A1* | 5/2010 | Jung | A61M 37/0015 604/272 |
| 2012/0027810 | A1* | 2/2012 | Chen | A61M 37/0015 424/400 |
| 2012/0220981 | A1* | 8/2012 | Soo | A61M 37/0015 604/506 |

FOREIGN PATENT DOCUMENTS

| JP | 2009195583 A | 9/2009 |
| JP | 2012505164 A | 3/2012 |
| KR | 10-0781702 B1 | 12/2007 |
| KR | 10-2012-0006293 A | 1/2012 |
| KR | 10-2012-0068516 A | 6/2012 |

OTHER PUBLICATIONS

Park et al., "Biodegradable polymer microneedles: Fabrication, mechanics and transdermal drug delivery", Journal of Controlled Release, 2005, vol. 104, No. 1, pp. 51-66.
Park JH et al., "Polymer Microneedles for Controlled-Release Drug Delivery", Pharmaceutical Research, 2006, vol. 23, No. 5, pp. 1008-1019.
Miyano et al., "Sugar Micro Needles as Transdermic Drug Delivery System", Biomedical Microdevices, 2005, vol. 7, No. 3, pp. 185-188.
Sullivan et al., "Minimally Invasive Protein Delivery with Rapidly Dissolving Polymer Microneedles", Advanced Materials, 2008, vol. 20, pp. 933-938.
Lee et al., "Dissolving microneedles for transdermal drug delivery", Biomaterials, 2008, vol. 29, pp. 2113-2124.

* cited by examiner

[Figure 1]
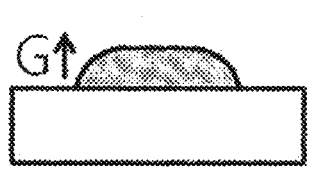 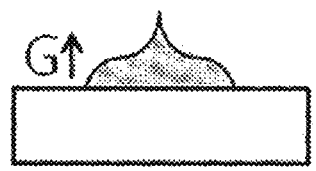 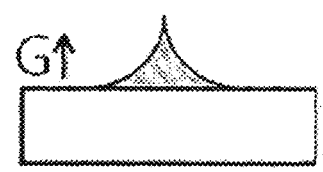
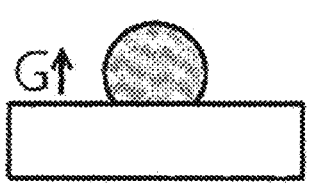 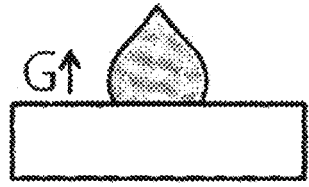 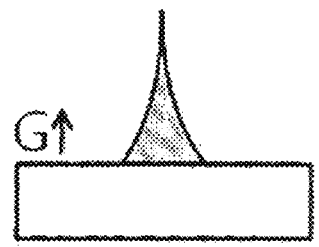

[Figure 2]
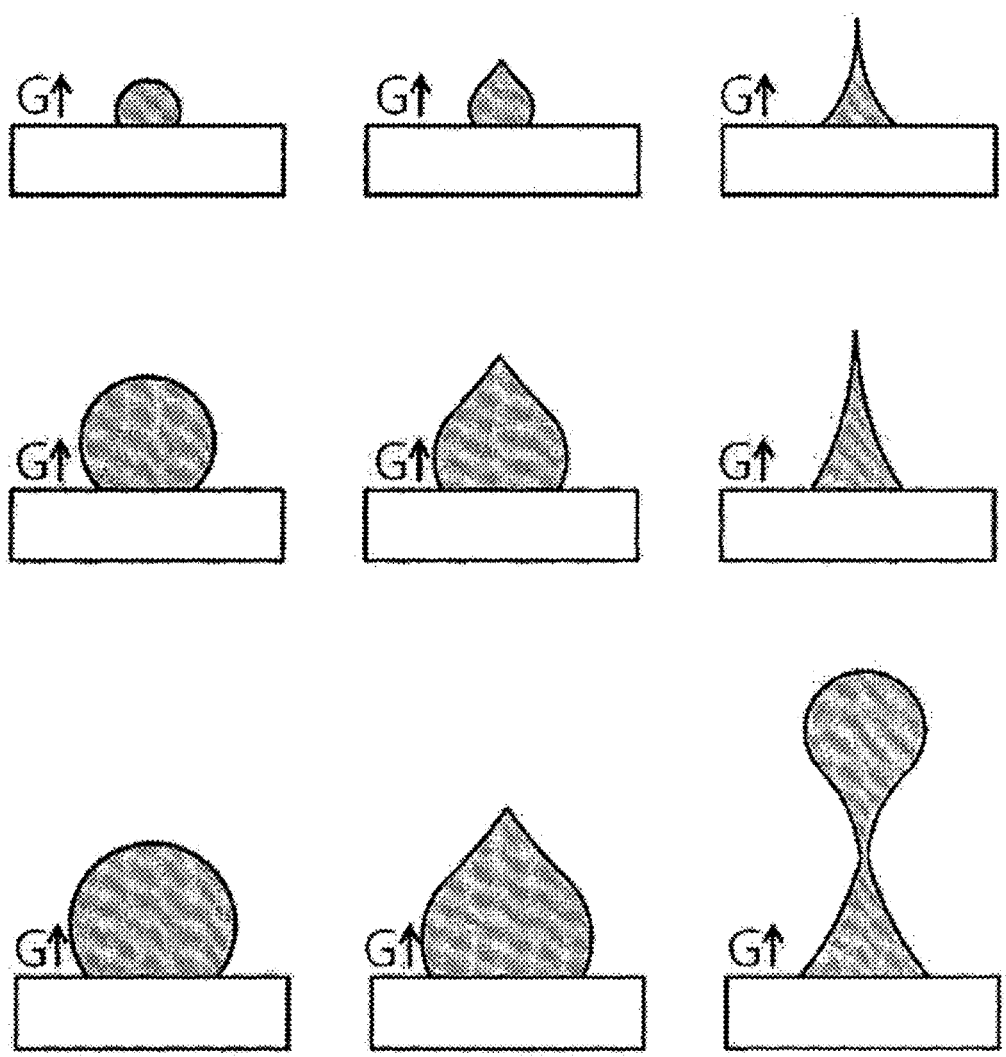

[Figure 3]
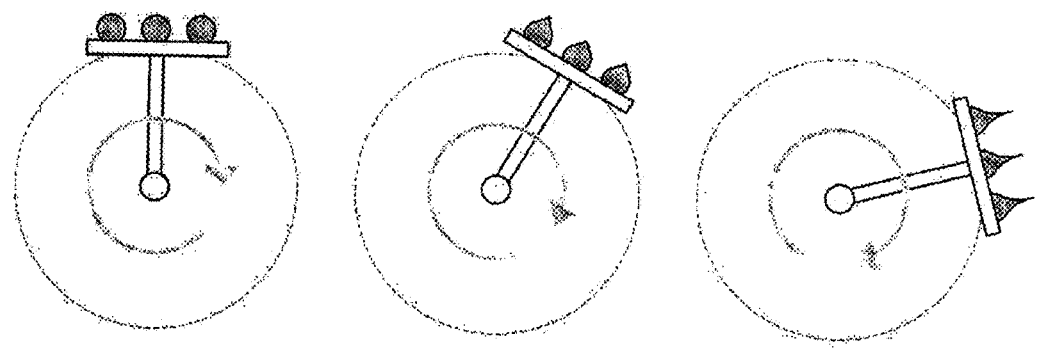

[Figure 4]
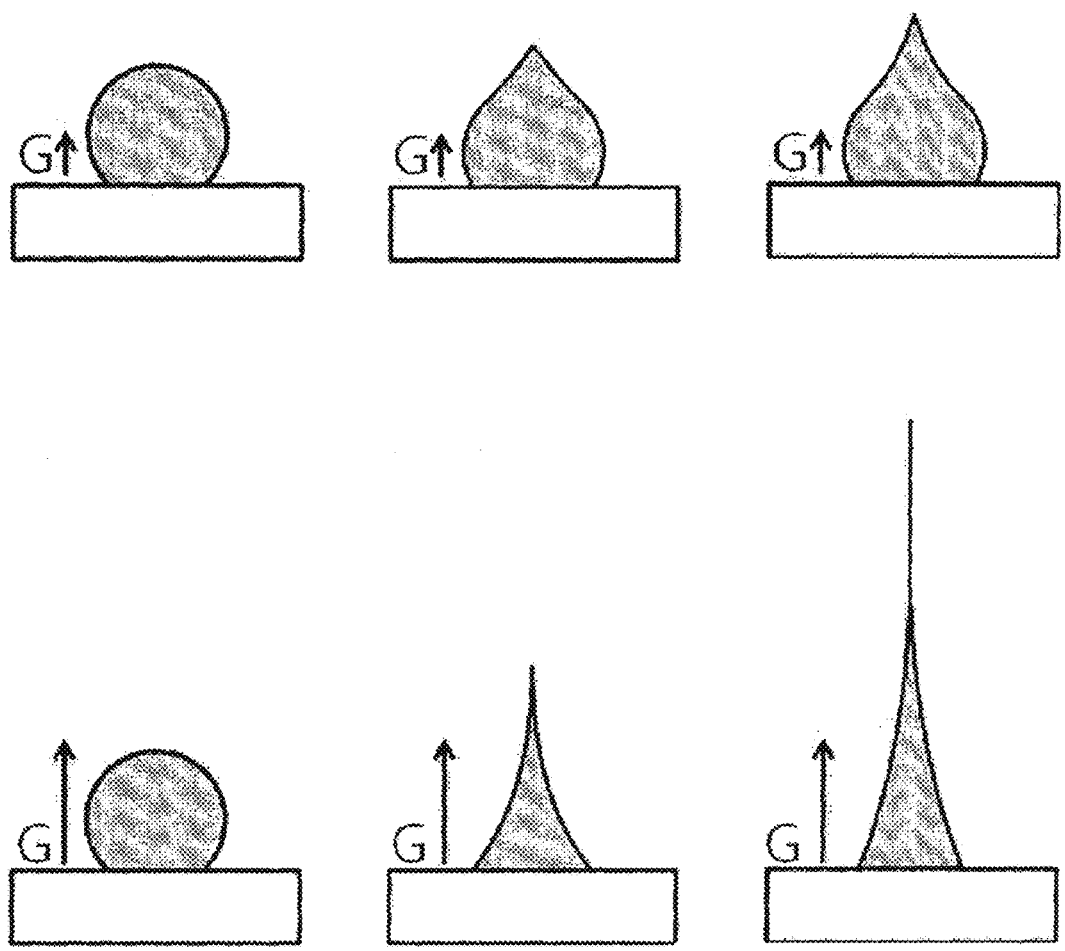

[Figure 5]
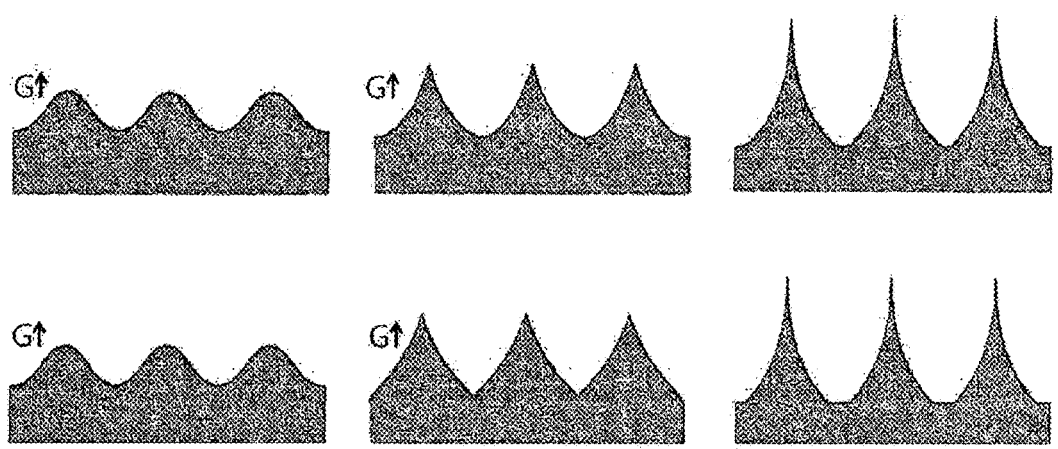

[Figure 6]
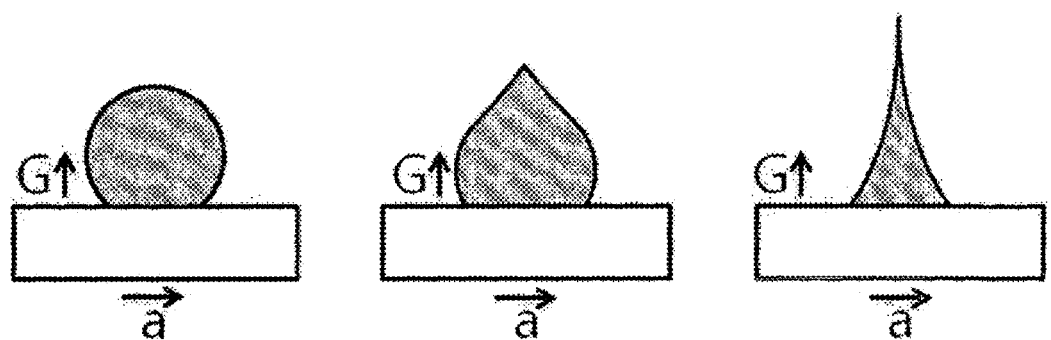
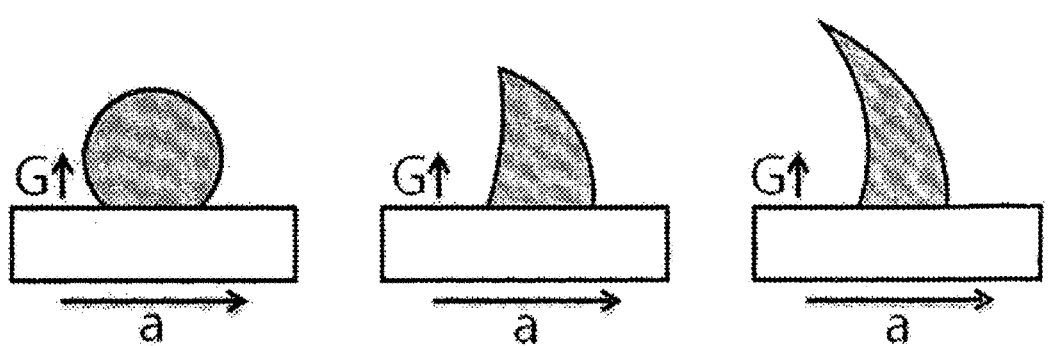

【Figure 7】
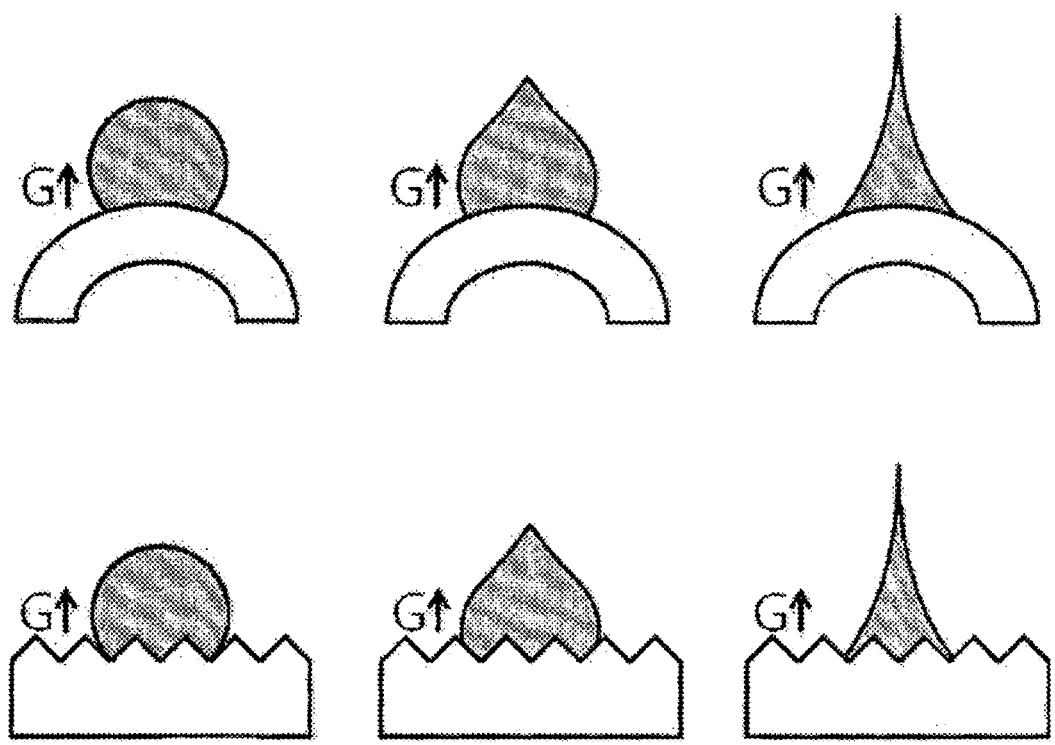

[Figure 8a]
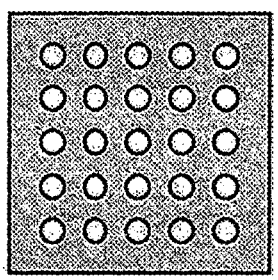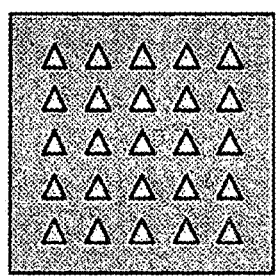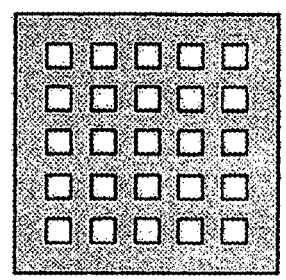

[Figure 8b]
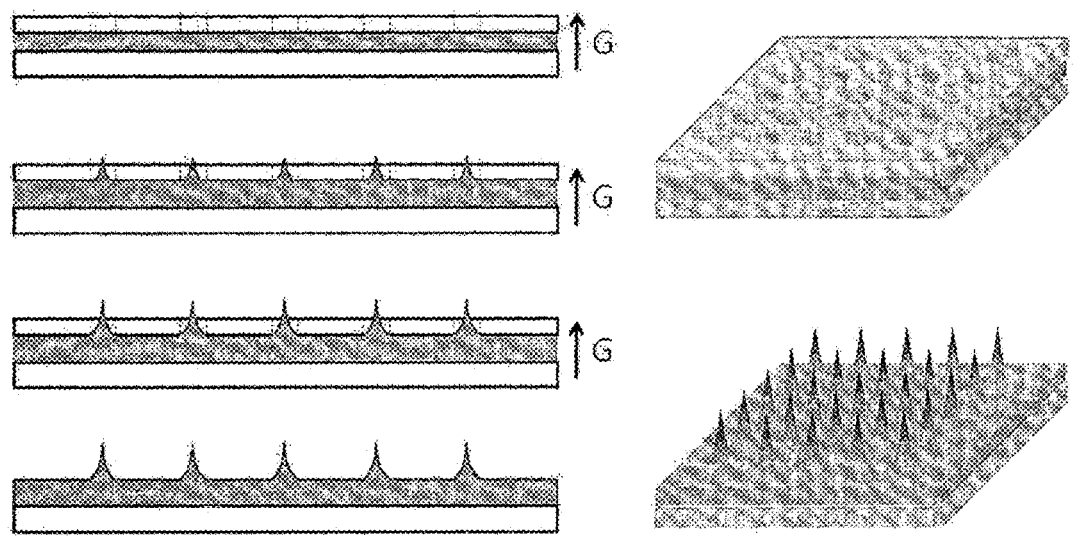

[Figure 9]
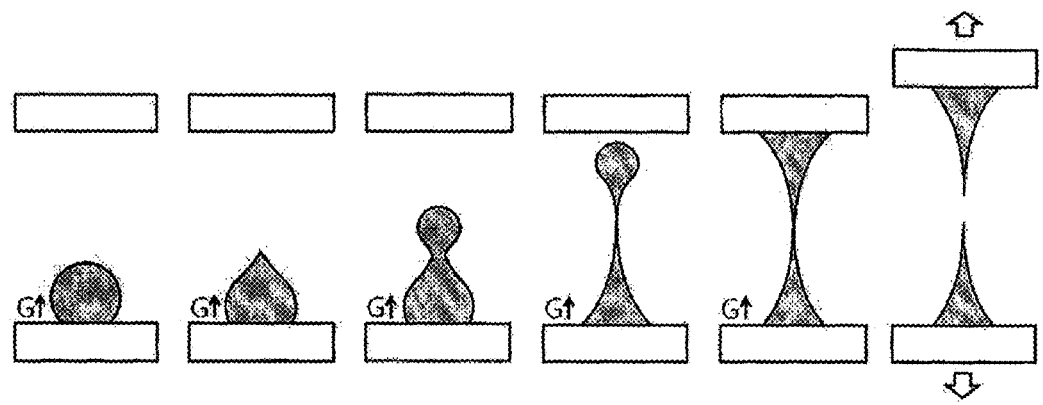

[Figure 10]
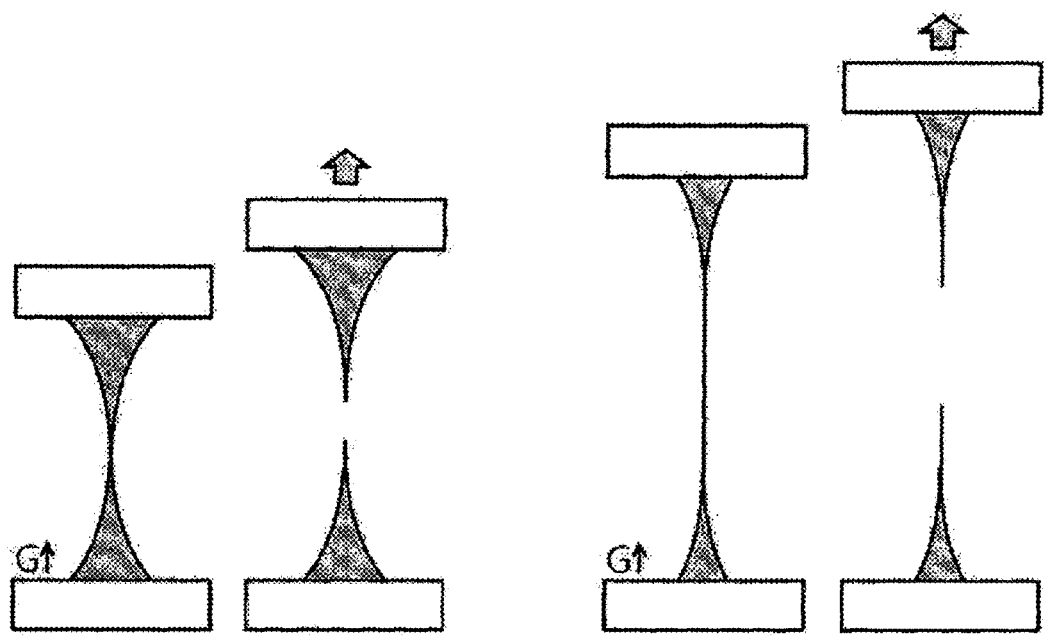

[Figure 11]
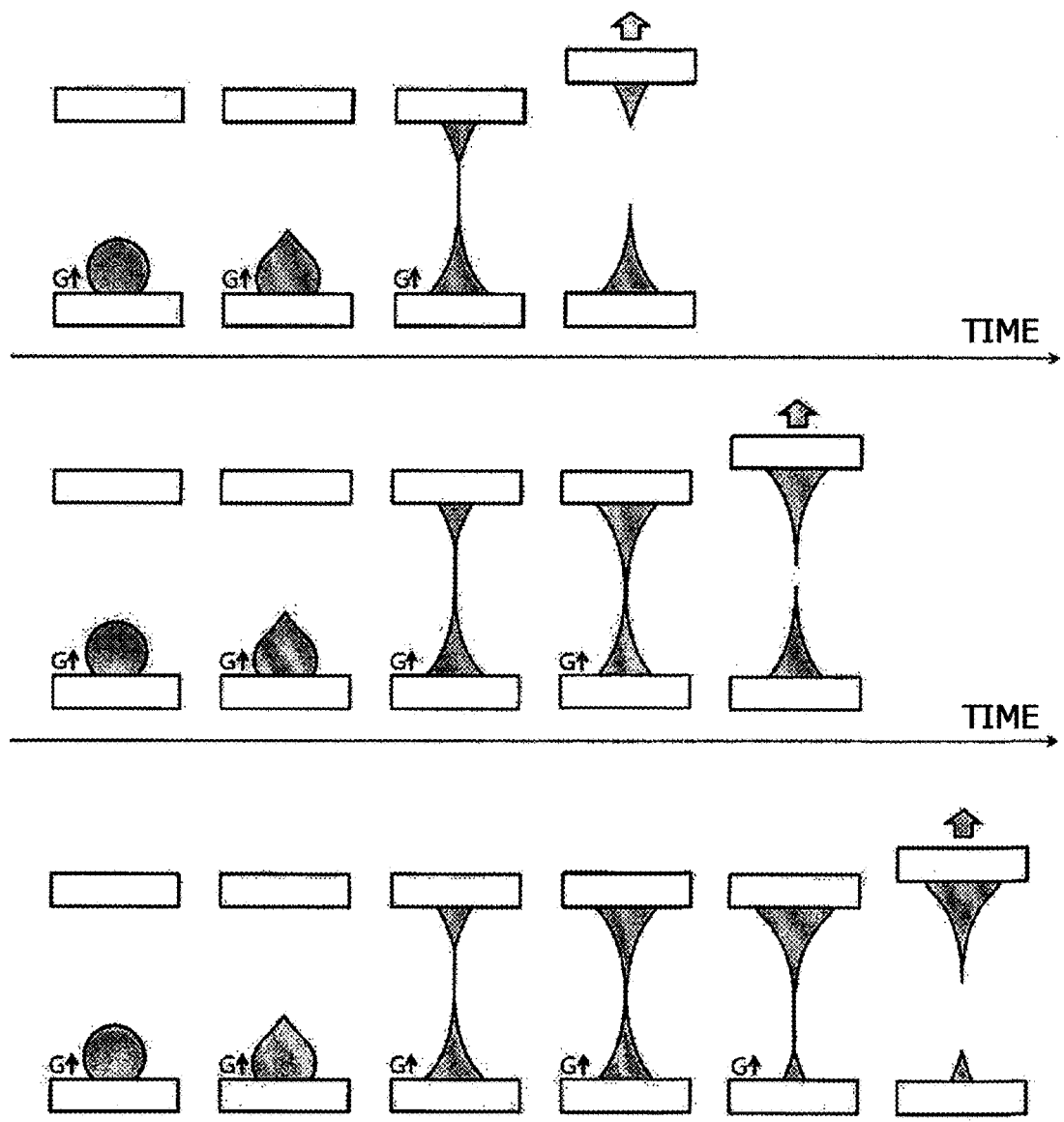

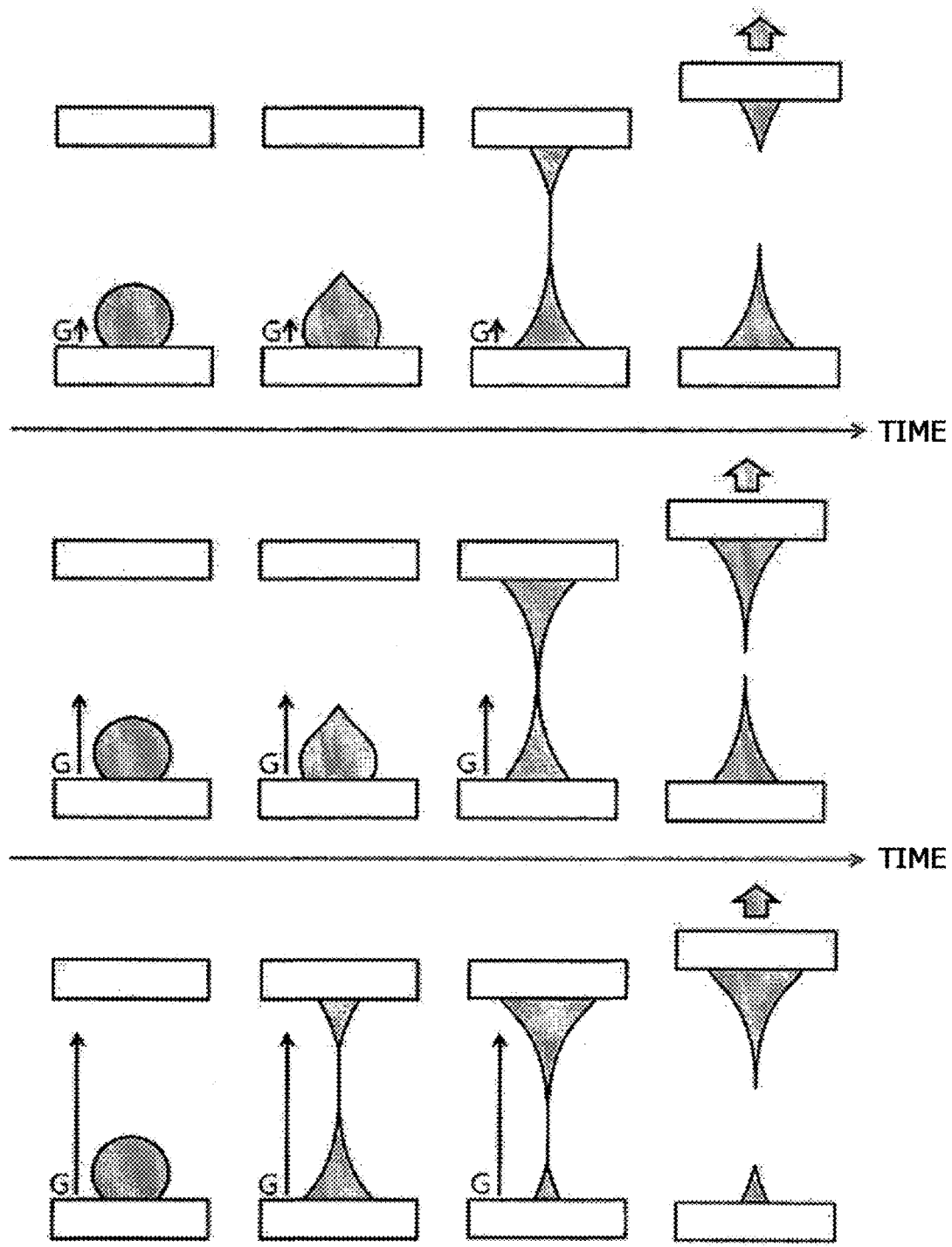
[Figure 12]

[Figure 13]
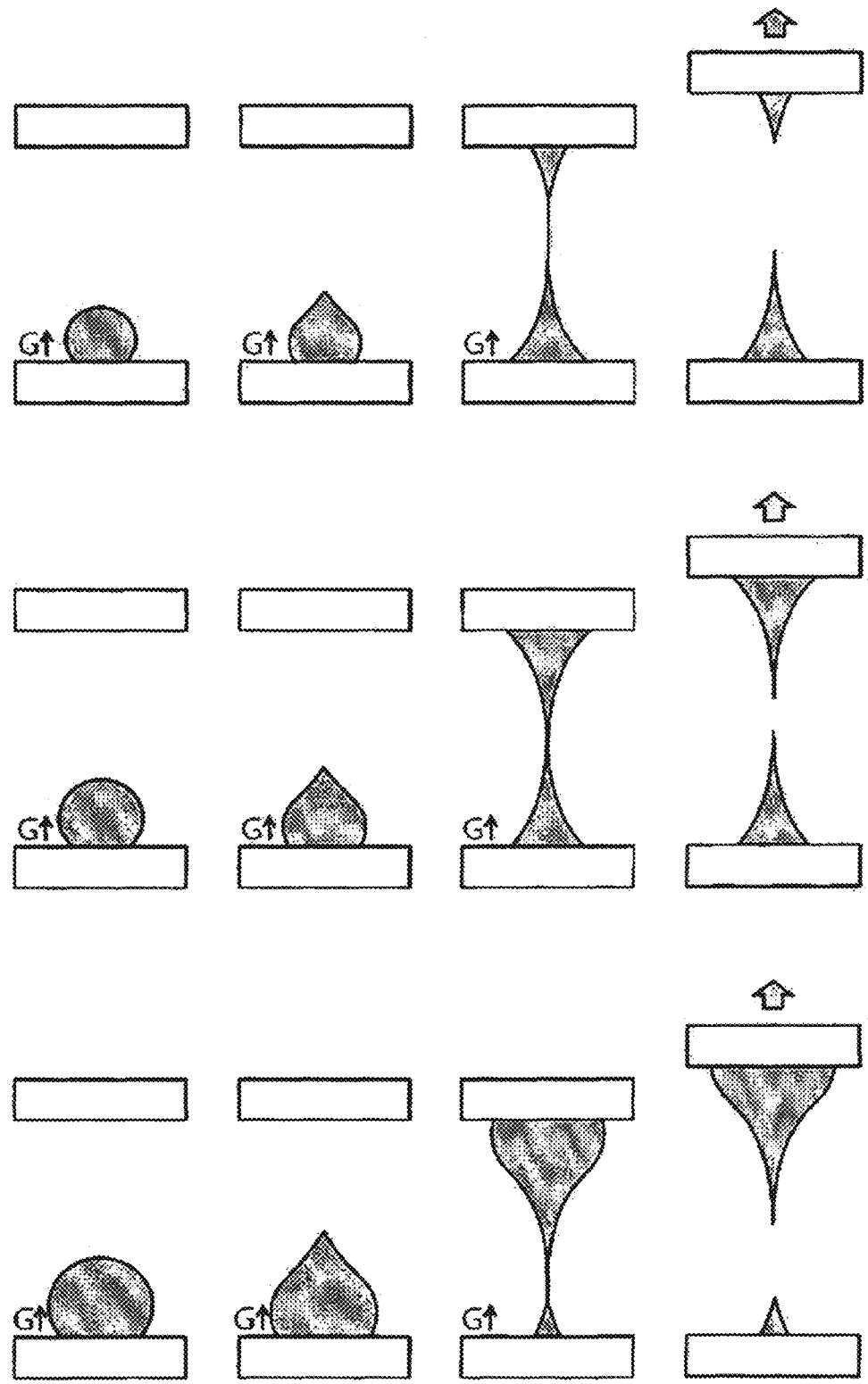

[Figure 14]
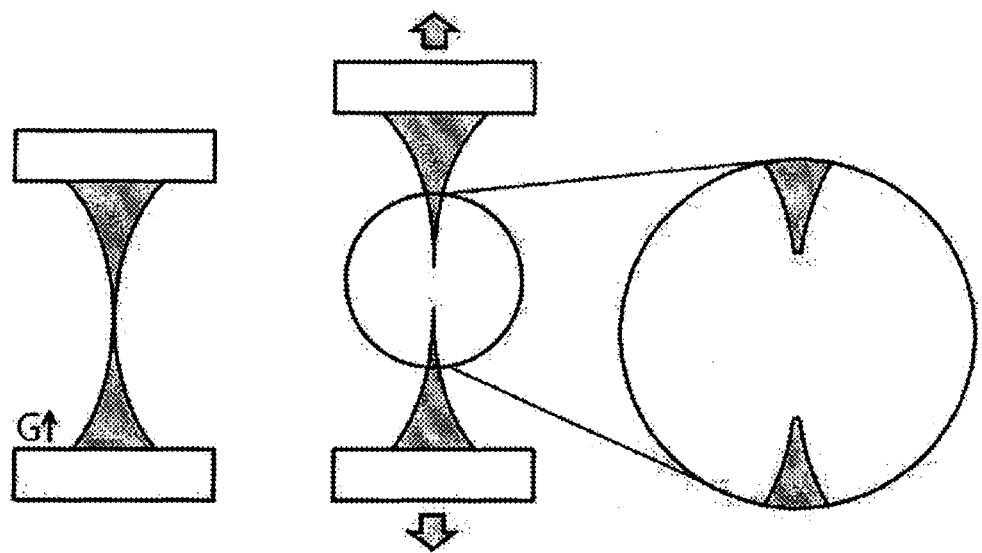
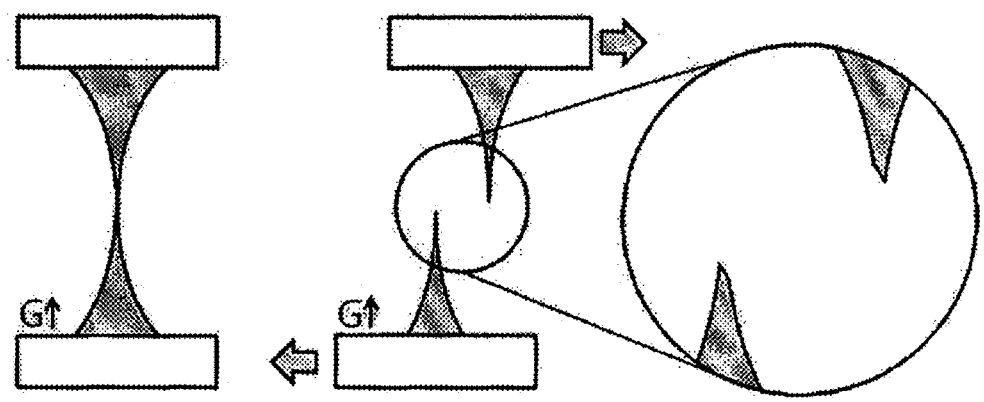

[Figure 15]
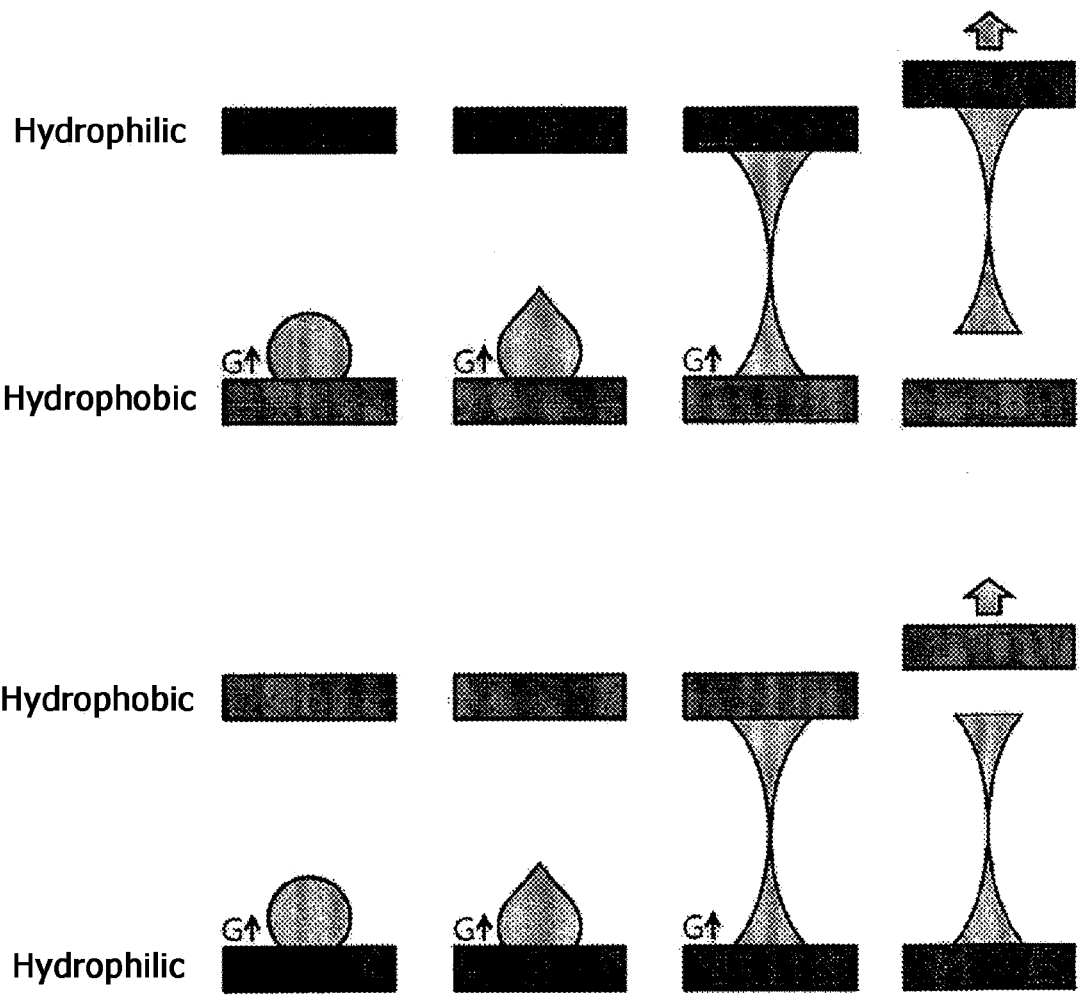

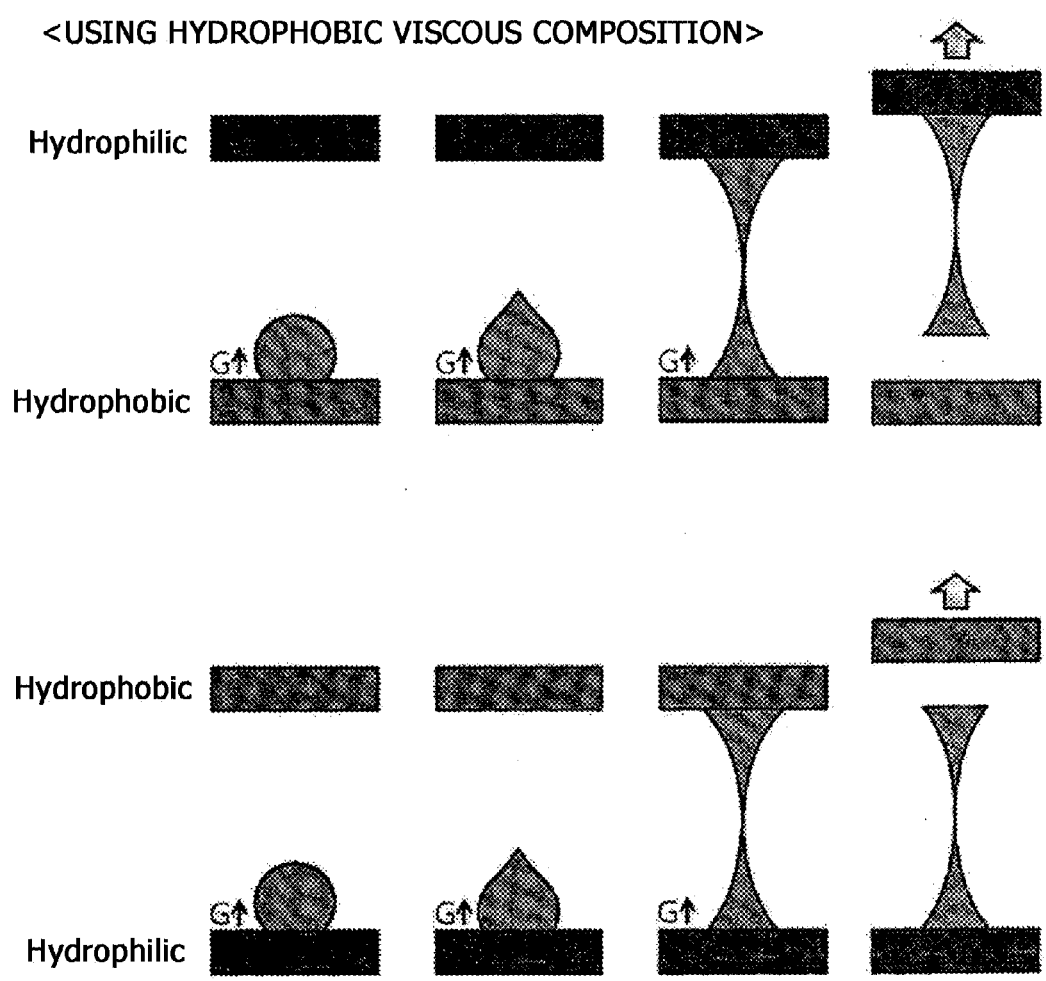
[Figure 16]

[Figure 17]
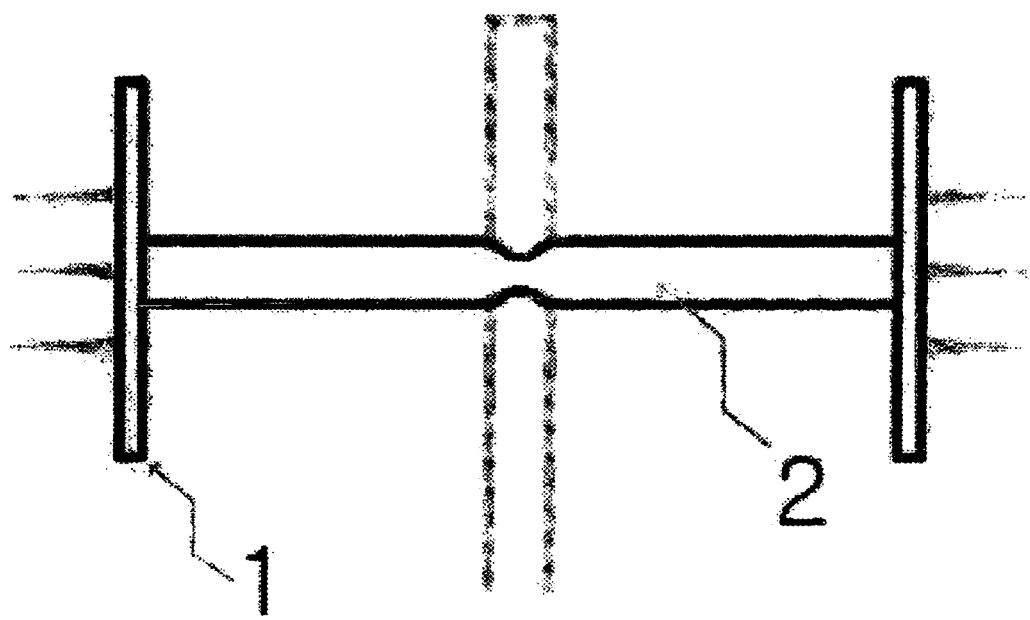

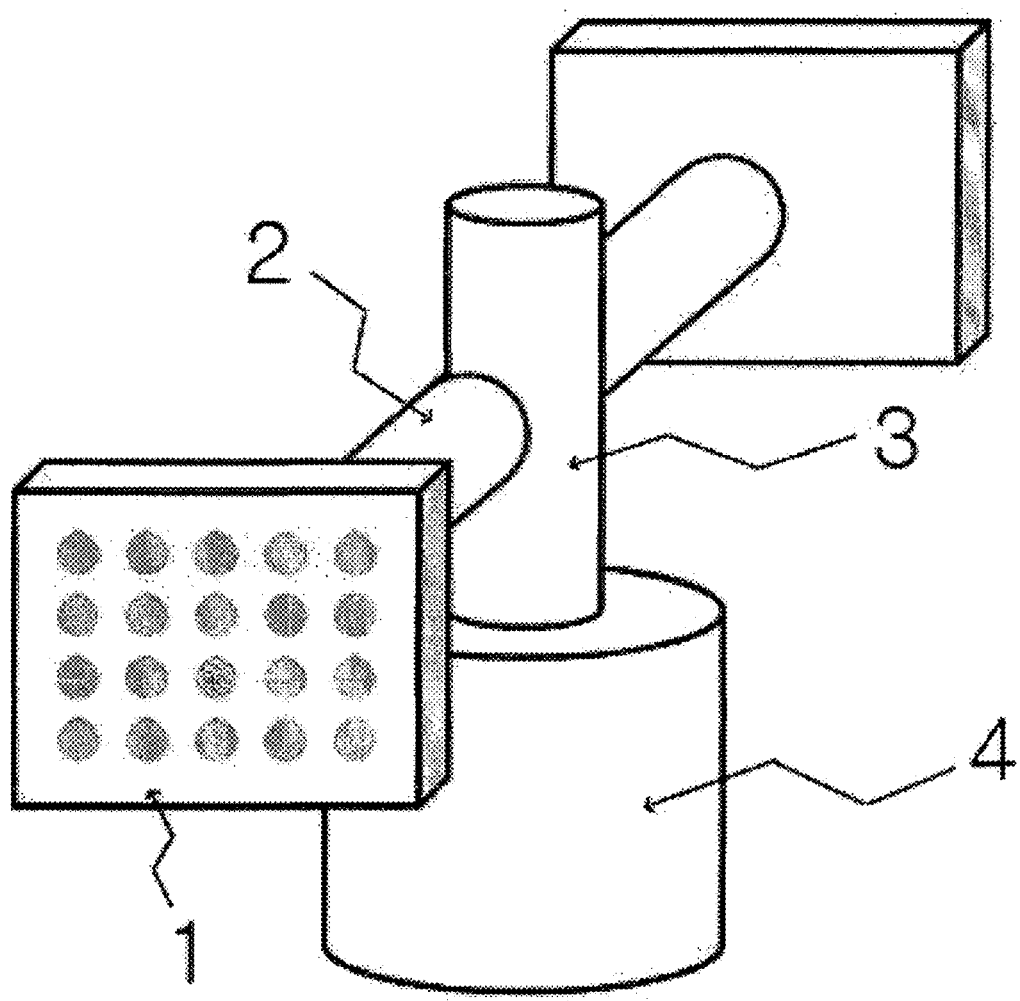
[Figure 18]

[Figure 19]
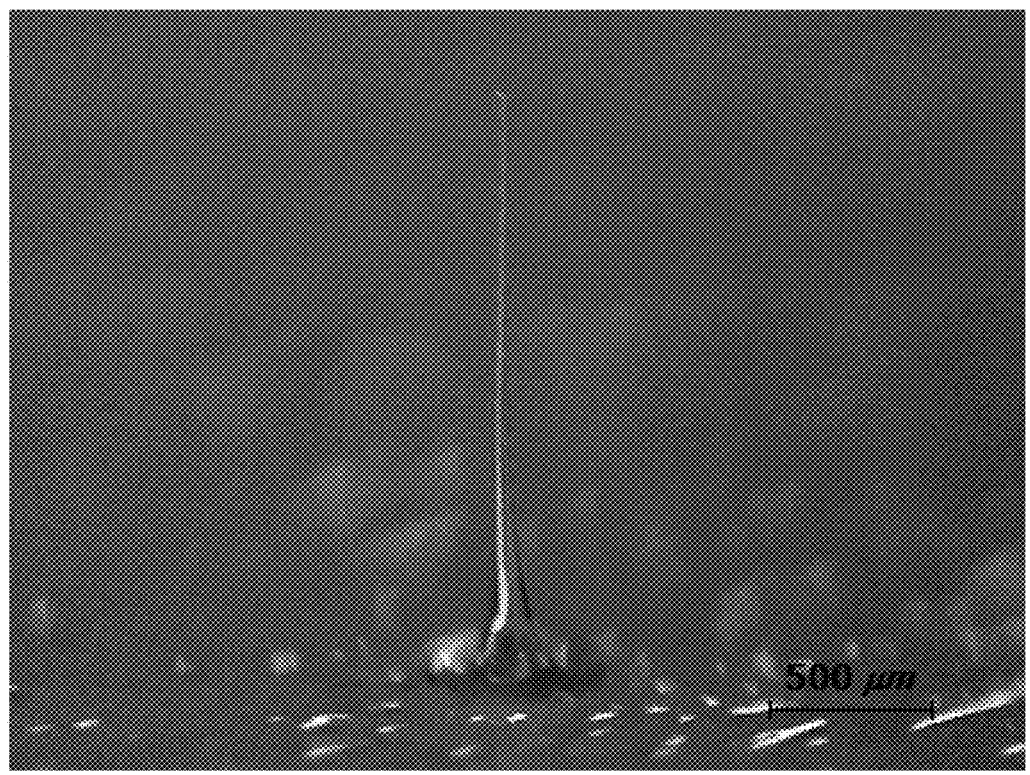

[Figure 20]
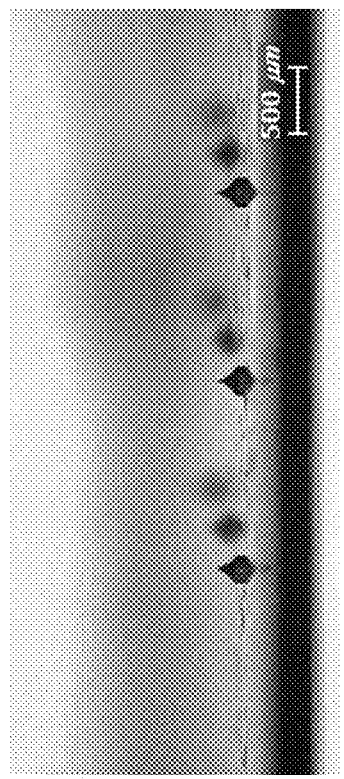
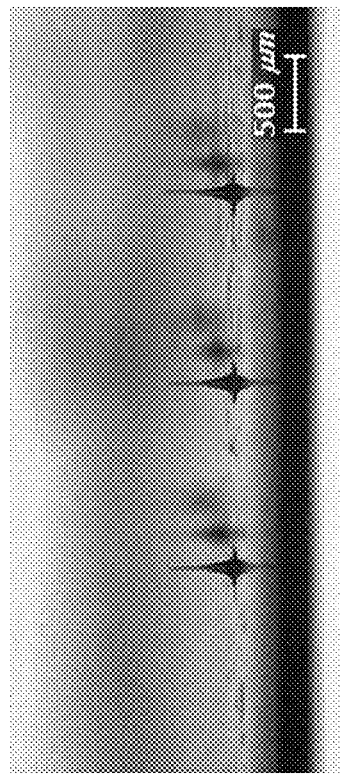

【Figure 21】
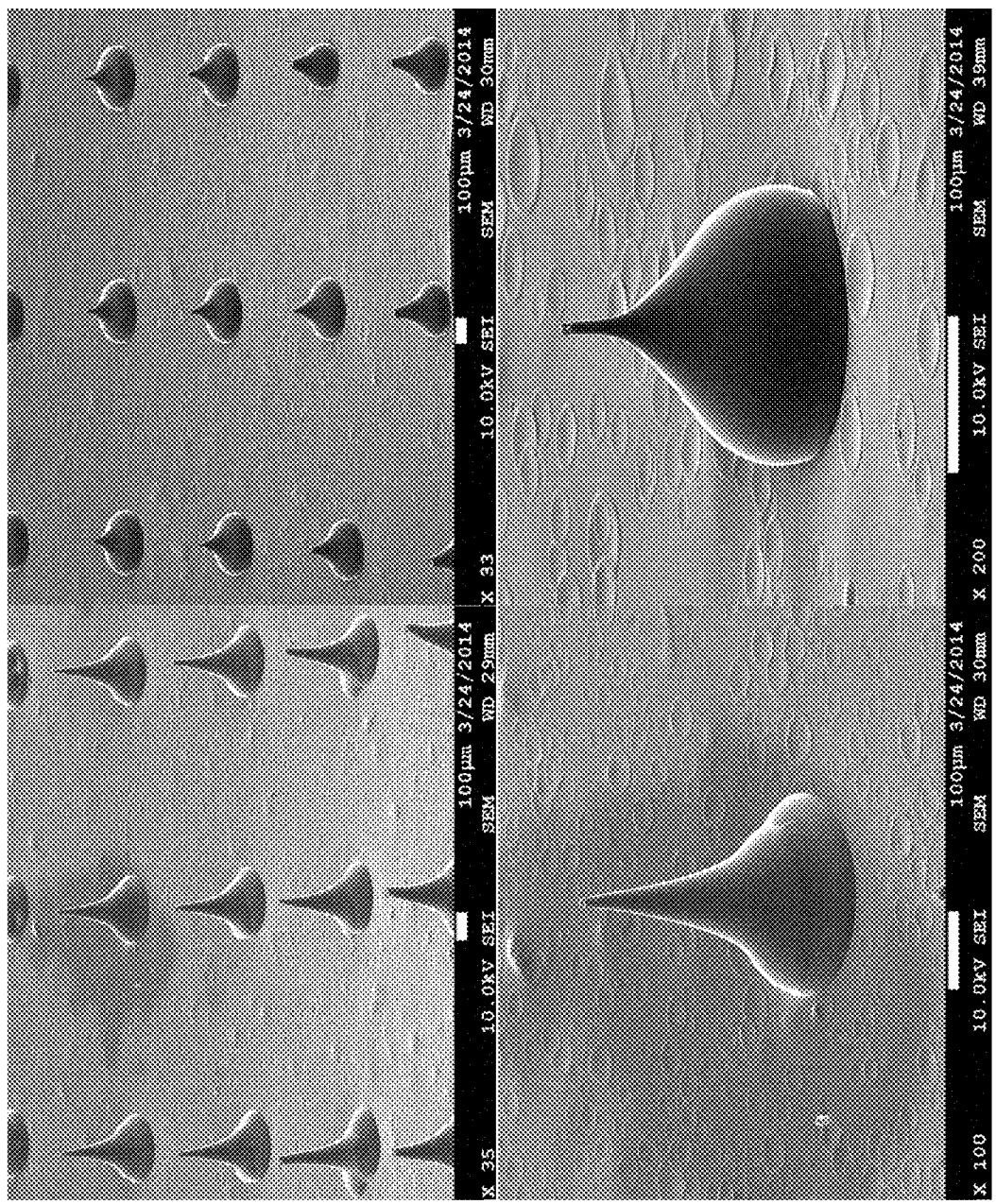

[Figure 22]
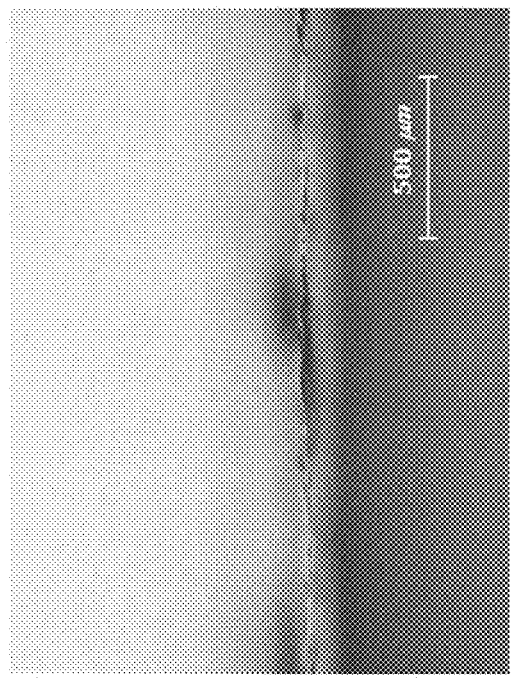
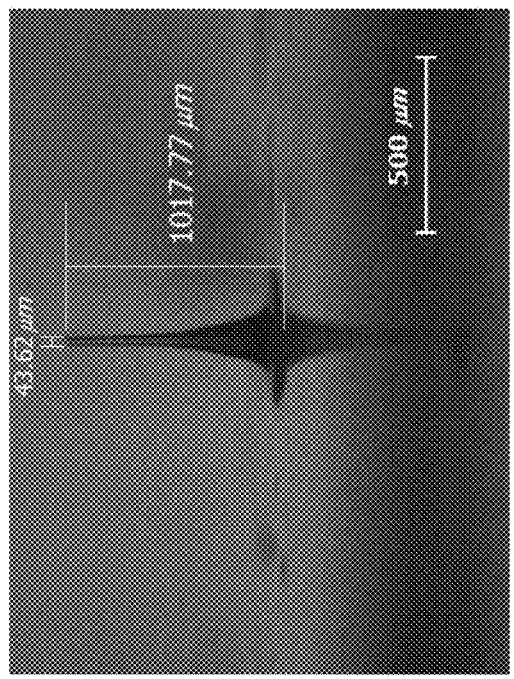

[Figure 23]
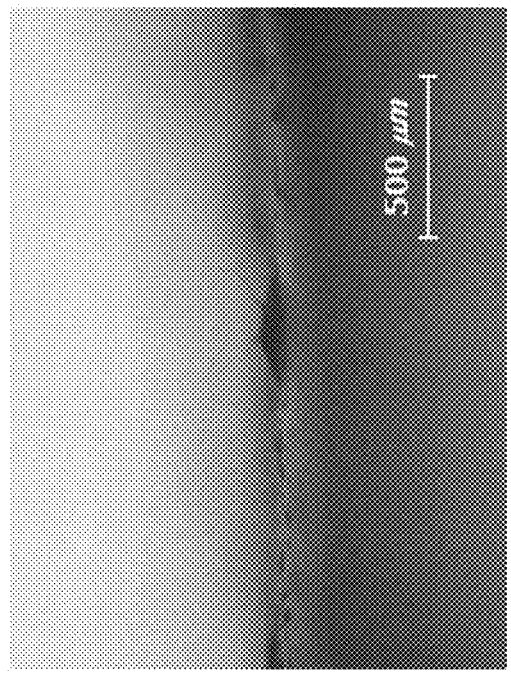
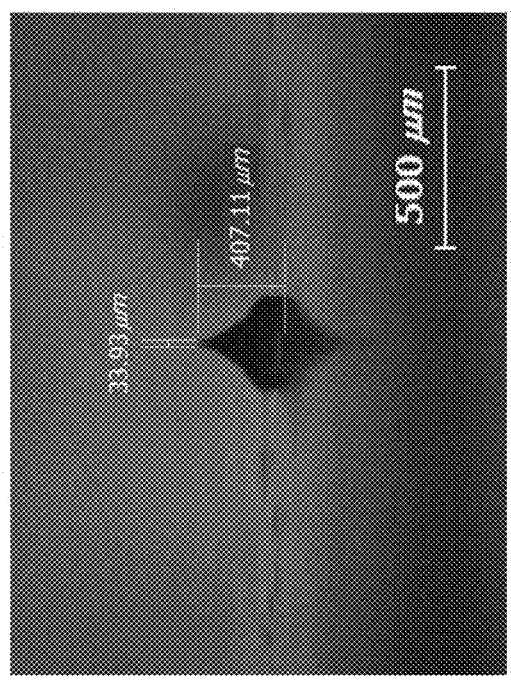

[Figure 24]
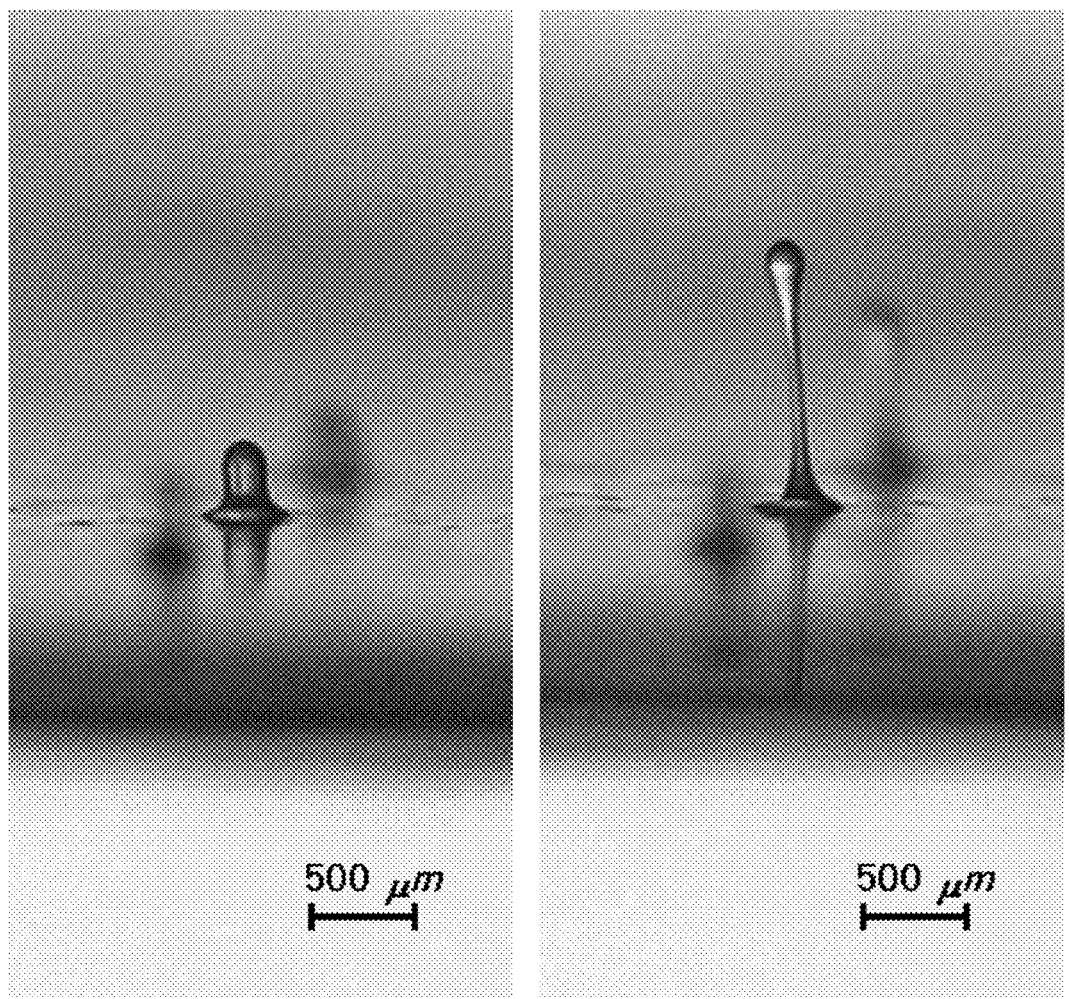

[Figure 25]
(A)
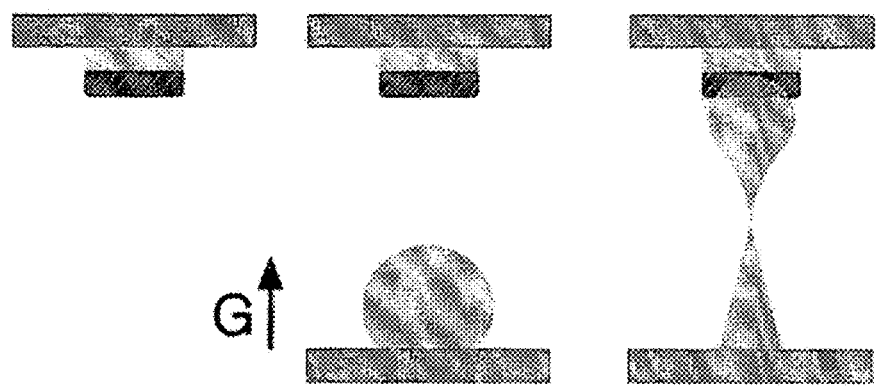
(B)
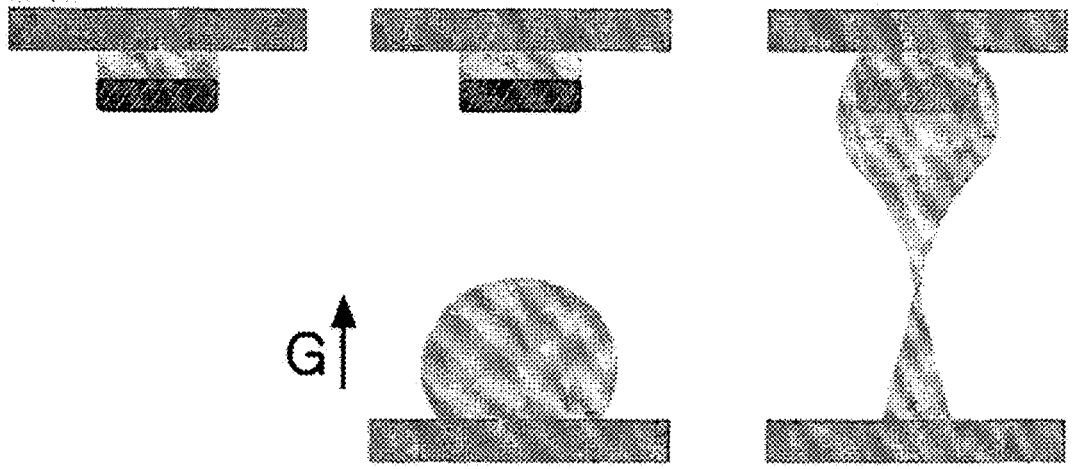

【Figure 26】
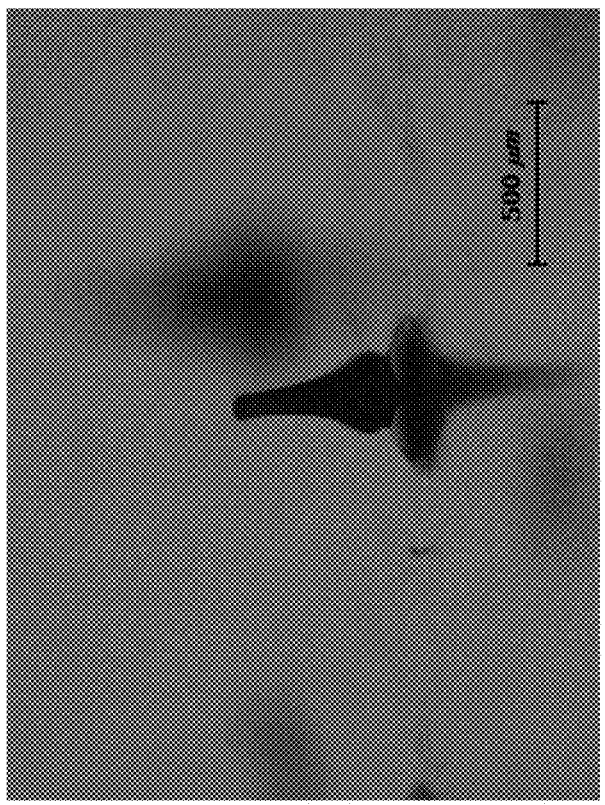
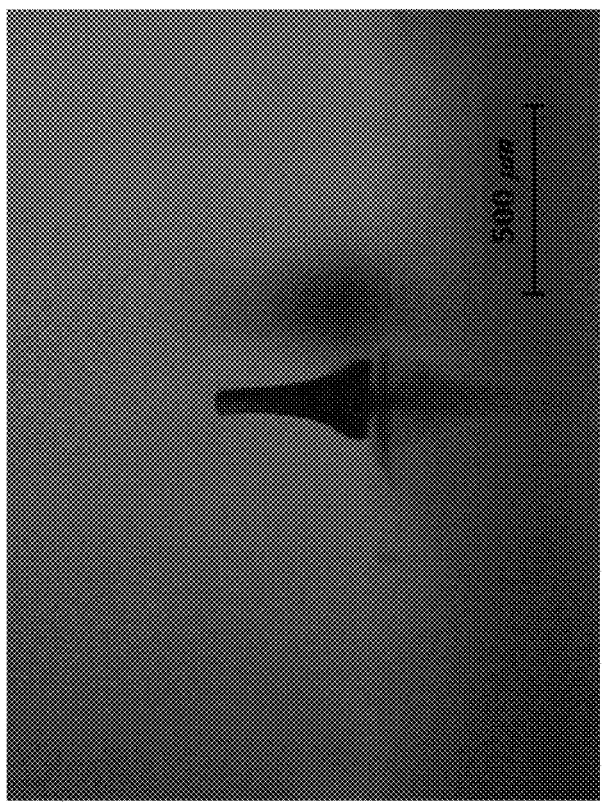

[Figure 27]
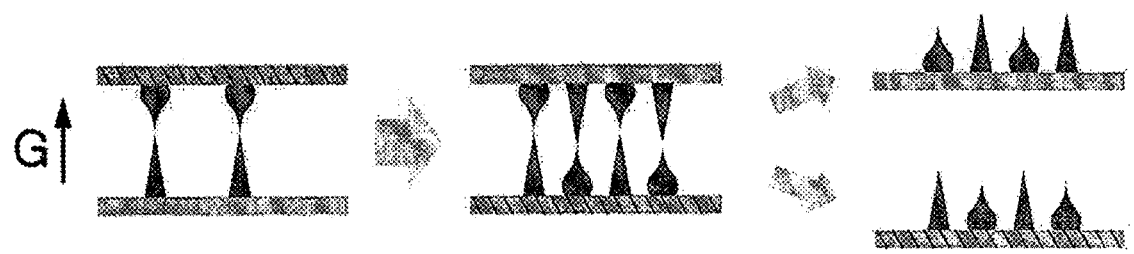

[Figure 28]
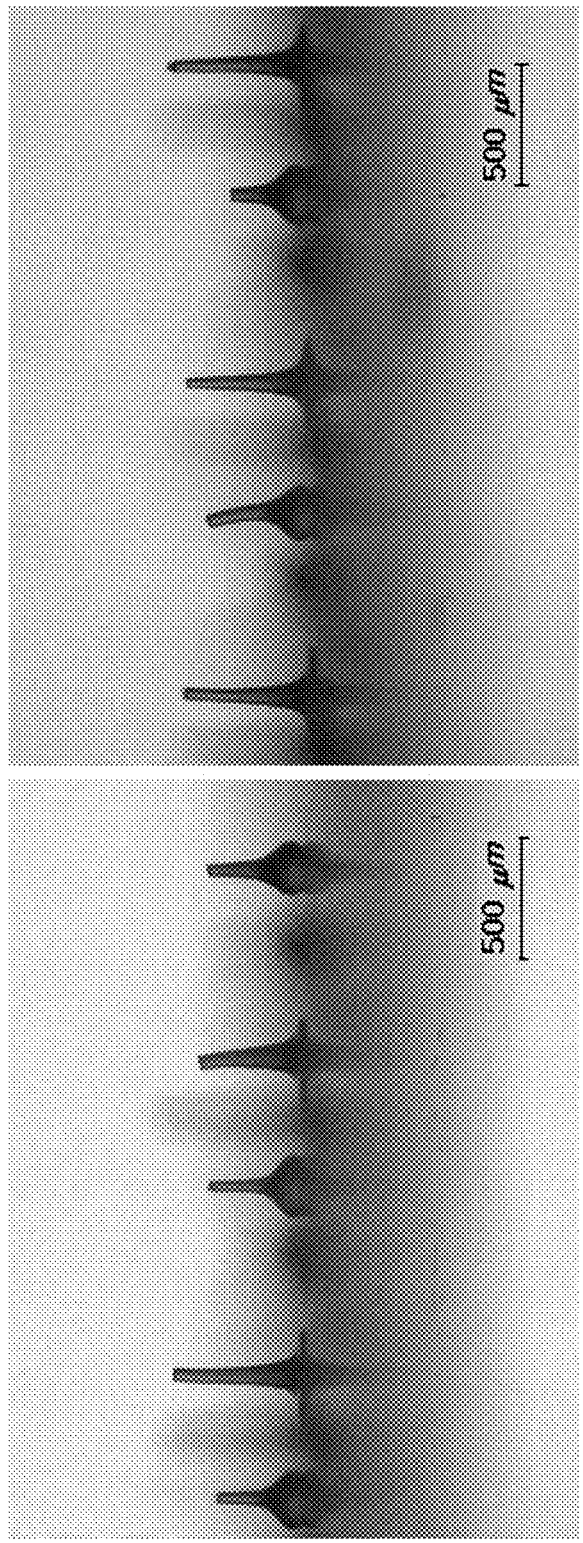

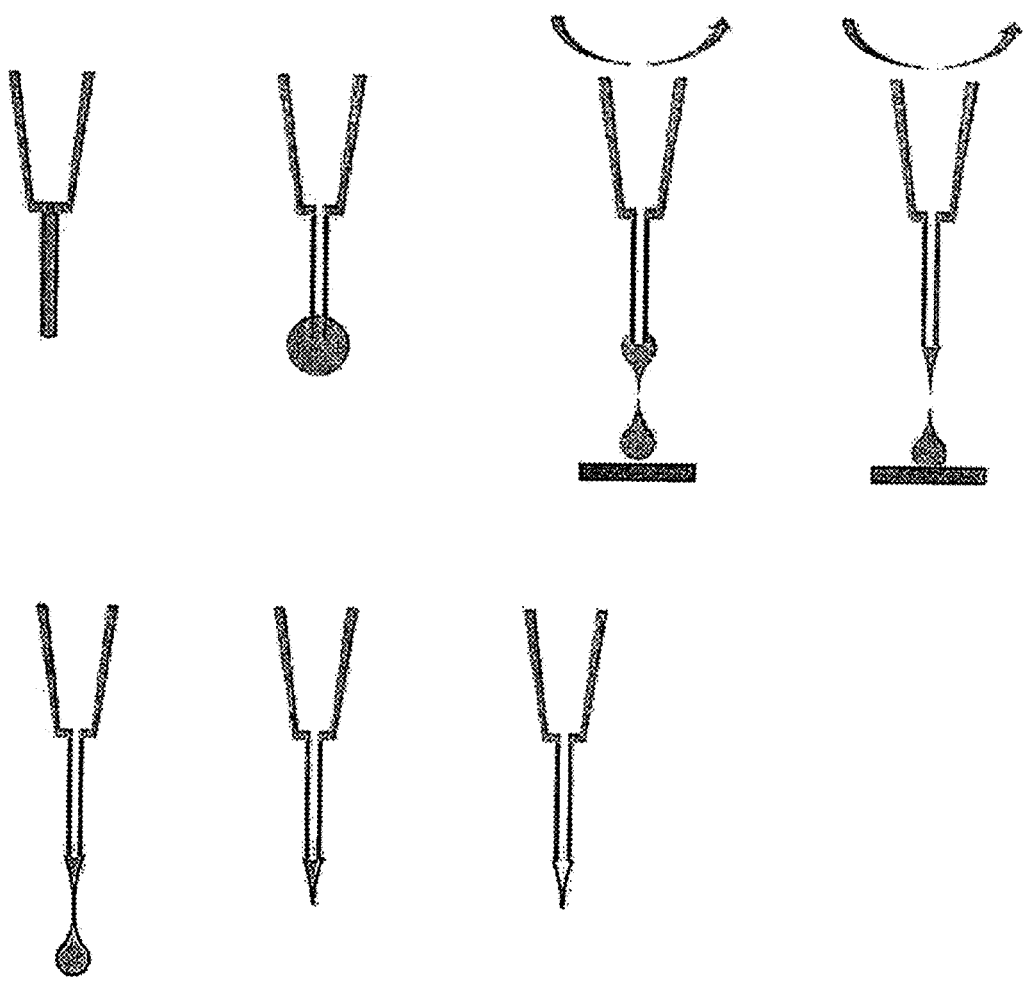
[Figure 29]

[Figure 30]
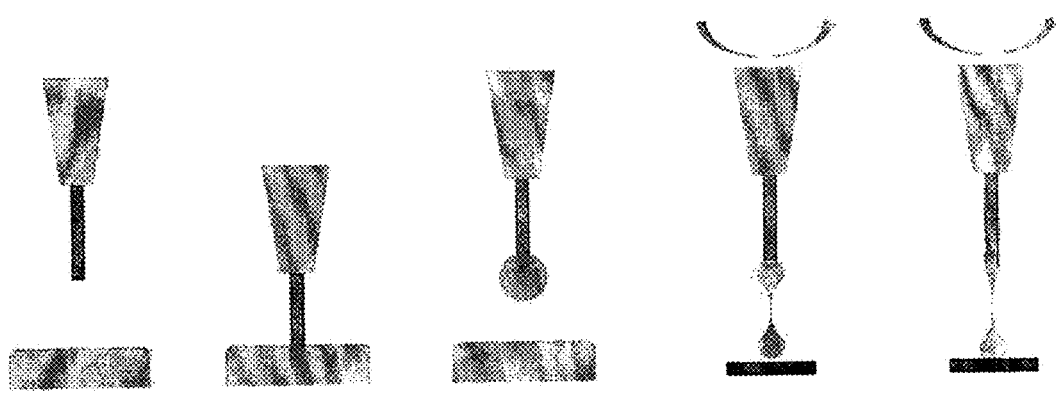

[Figure 31]
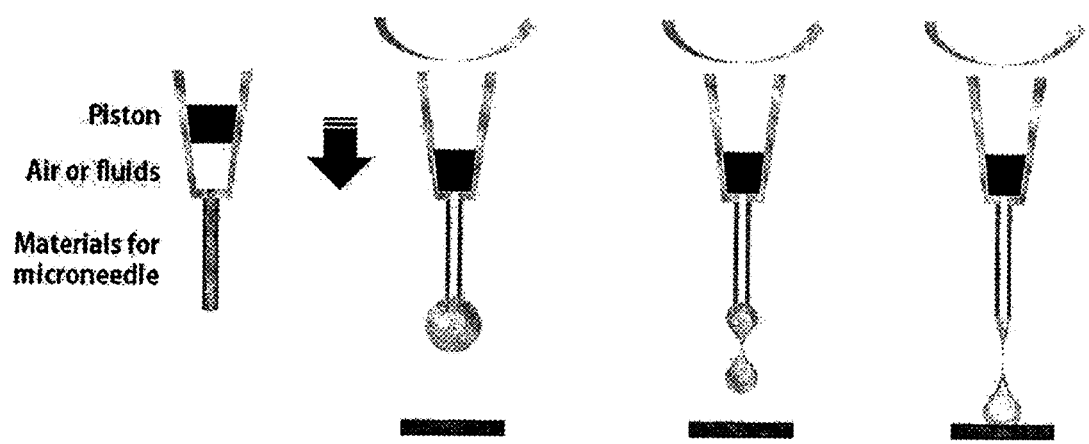

METHOD FOR MANUFACTURING MICROSTRUCTURE USING CENTRIFUGAL FORCE AND MICROSTRUCTURE MANUFACTURED BY SAME

TECHNICAL FIELD

This application claims priority to and the benefit of Korean Patent Application No. 10-2013-0050462, filed on May 6, 2013, the disclosure of which is incorporated herein by reference in its entirety.

The present invention relates to a method for manufacturing a microstructure using a centrifugal force and the microstructure manufactured by the same.

BACKGROUND ART

Even though numerous drugs and therapeutic agents, etc. for treating diseases have been developed, a problem of penetrating a biological barrier (such as barriers of skin, oral mucosa, and brain blood vessels) and a problem of efficiency in drug delivery still remain as points to be improved.

A drug is generally administered orally in a refined or capsule form. However, numerous drugs cannot be effectively delivered only by the above administration method since the drugs disappear due to being digested or absorbed in a gastrointestinal tract or a mechanism of a liver. Furthermore, some drugs cannot be diffused effectively after penetrating an intestinal mucous membrane. In addition, compliance of a patient also becomes a problem (for example, when a patient needs to take a drug at specific intervals or in case of a critical patient who cannot take a drug).

Another common technology in drug delivery is using a conventional needle. While a method using the conventional needle is effective compared to oral administration, it has a problem of causing pain at an injection site, local damage of skin, disease infection at bleeding and injection sites, etc.

To solve the above problems, various microstructures including a microneedle have been developed. The microneedle developed so far has been mostly used in delivering a drug in a body, collecting blood, detecting a substance to be analyzed in a body, etc. Unlike the conventional needle, the microneedle is characterized by painless skin penetration and no external damage, and a diameter of a top portion of the microneedle for minimal pricking is important in painless skin penetration. In addition, since the microneedle has to penetrate a stratum corneum of 10-20 μm, which is the strongest obstacle in skin, the microneedle needs to have sufficient physical hardness. In addition, a proper length of the microneedle for improving drug delivery efficiency by reaching a capillary vessel should also be considered.

Various types of microneedles were developed after an in-plane type microneedle (Lin Liwei et al., "Silicon-processed Microneedles", *Journal of microelectromechanical systems: a joint IEEE and ASME publication on microstructures, microsensors, and microsystems* 8(1): 78-84 (1999)) was previously suggested. A method for fabricating an out-of-plane type solid microneedle (U.S. Patent Application Disclosure No. 2002138049, "Microneedle devices and methods of manufacture and use thereof") using etching manufactures a solid silicone microneedle with a diameter of 50-100 μm and a length of 500 μm, thus being unable to realize painless skin penetration and having a difficulty in delivering a drug or a cosmetic component to a target site.

Meanwhile, Prausnitz of University of Georgia in the U.S. has suggested a method for fabricating a biodegradable polymer microneedle by etching glass or forming a mold using photolithography (Jung-Hwan Park et al., "Biodegradable polymer microneedles: Fabrication, mechanics and transdermal drug delivery," *Journal of Controlled Release* 104(1): 51-66 (2005)). In addition, in 2006, a method for fabricating a biodegradable solid microneedle by mounting a substance fabricated in a capsule form on an end of the mold fabricated by a photolithography method was suggested (Park J H et al., "Polymer Microneedles for Controlled-Release Drug Delivery," *Pharmaceutical Research* 23(5): 1008-19 (2006)). When this method is used, a drug that can be fabricated in a capsule form may be freely mounted, but there is a limitation in application to a drug that needs to be administered in a large amount since hardness of a microneedle weakens when an amount of a mounted drug increases.

In 2005, an absorption type microneedle was suggested by Nano Device and Systems Inc. (Japanese Patent Application Disclosure No. 2005154321; and Takaya Miyano et al., "Sugar Micro Needles as Transdermic Drug Delivery System," *Biomedical Microdevices,* 7(3): 185-188(2005)). The above absorption type microneedle is to be used in drug delivery or cosmetic care by being inserted in skin and not removed. In this method, a microneedle was fabricated by applying a composition in which maltose is mixed with a drug to a mold and coagulating the composition. The Japanese patent suggests transdermic drug delivery by fabricating the absorption type microneedle, but the microneedle caused pain when penetrating skin. In addition, due to a technical limitation of mold fabrication, it was impossible to fabricate a microneedle that has a proper top portion diameter causing no pain and a length in a range required for effective drug delivery, i.e. a length equal to or greater than 1 mm.

A biodegradable microneedle that was fabricated by Prausnitz of University of Georgia in the U.S. was fabricated in a polydimethylsiloxane (PDMS) mold using a substance in which polyvinylpyrrolidone (PVP) and methacrylic acid (MAA) were mixed (Sean P Sullivan et al., "Minimally Invasive Protein Delivery with Rapidly Dissolving Polymer Microneedles," *Advanced Materials* 20(5): 933-938(2008)). In addition, a microneedle was also fabricated by putting carboxymethyl cellulose in a pyramidal mold (Lee J W et al., Dissolving microneedles for transdermal drug delivery, *Biomaterials* 29(13): 2113-24 (2008)). Despite their advantage of being able to rapidly, easily, and conveniently fabricate a microneedle, the methods using molds have not succeeded in overcoming their limitation of being difficult to fabricate a microneedle with an adjusted diameter and length of the microneedle.

Skin is formed of the stratum corneum (<20 μm), an epidermis (<100 μm), and a dermis (300-2,500 μm). Therefore, to deliver a drug and a skin care component to a specific skin layer without causing pain, fabricating a microneedle to have a diameter of a top portion within 30 μm, an effective length of 200-2,000 μm, and sufficient hardness for skin penetration is effective in delivering the drug and the skin care component. In addition, to deliver a drug or a cosmetic component, etc. through a biodegradable solid microneedle, any process that may destroy activation of the drug or the cosmetic component, such as a high-temperature treatment, an organic solvent treatment, etc., should be avoidable in a process of manufacturing a microneedle.

A method for manufacturing a microstructure using a conventional mold is the most commonly-used manufacture method. However, the manufacture method using the mold has a limitation in which loss occurs in a process of separating the mold. This is due to a damage of a fabricated microstructure which occurs in a process of separating the microstructure from the mold by a contact force between the microstructure manufactured in the mold and the mold. In addition, the method for manufacturing the microstructure using the mold has a limitation of not being able to fabricate a microstructure with a large aspect ratio. This limitation is caused by a difficulty of filling a viscous composition into a micro-mold having a large aspect ratio.

In addition, a method for manufacturing a microstructure by extending a viscous composition through contact with a pillar or a substrate is a fabrication method that is capable of fabricating a structure with a relatively high aspect ratio. However, loss in a process of separating the structure also occurs in this method. In addition, flatness of the pillar or the substrate determines a degree of contact with the viscous composition, which causes a limitation in fabrication yield of a microstructure. That is, due to a difficulty of maintaining the flatness, uniformity and yield of the fabricated microstructure are lowered.

The present inventors have tried to overcome problems of the prior art through completion of the present invention.

Throughout the present specification, several papers and patent documents are used as references, and the citations thereof are indicated. The disclosure of the cited papers and patent documents is incorporated in the present specification by reference in its entirety, to describe a level of a technical field to which the present invention pertains and content of the present invention more clearly.

DISCLOSURE

Technical Problem

The present inventors have tried to develop a solid microstructure which has a micro-unit diameter and a sufficient effective length and hardness while being able to easily contain heat-sensitive drugs without spoilage or inactivation of the drugs. As a result, the present inventors have developed a method for manufacturing a microstructure by applying a centrifugal force to a viscous composition and inducing an extension of the viscous composition. According to the method, the present invention was completed by (i) providing a microstructure having a micro-unit diameter and a sufficient effective length and hardness; (ii) avoiding any process that may destroy activation of a drug or a cosmetic component, such as high-temperature treatment, organic solvent treatment, etc; (iii) reducing loss resulting from contact and separation; (iv) overcoming a limitation of aspect ratio of a manufactured microstructure; (v) overcoming a limitation of yield resulting from flatness; and (vi) confirming that manufacturing microstructures of various shapes is possible.

Therefore, an aspect of the present invention is to provide a method for manufacturing a microstructure.

Another aspect of the present invention is to provide the microstructure manufactured by the method.

Still another aspect of the present invention is to provide an apparatus for manufacturing the microstructure.

Other aspects and advantages of the present invention will become clear by detailed descriptions, claims, and drawings of the invention below.

Technical Solution

According to an aspect of the present invention, the present invention provides a method for manufacturing a microstructure which includes the following steps:

(a) preparing a viscous composition on a lower substrate; and (b) applying a centrifugal force to the viscous composition to induce an extension of the viscous composition, thereby manufacturing a microstructure.

The present inventors have tried to develop a new method for manufacturing a microstructure which solves the above-mentioned problems of the prior art while having the following advantages: (i) providing a microstructure having a micro-unit diameter and sufficient effective length and hardness, (ii) avoiding any process that may destroy activation of a drug or cosmetic component, such as high-temperature treatment, organic solvent treatment, etc., (iii) reducing loss resulting from contact and separation, (iv) overcoming a limitation of aspect ratio of a manufactured microstructure, (v) overcoming a limitation of yield resulting from flatness, and (vi) manufacturing a microstructure of various shapes is possible. As a result of study, it was confirmed that a microstructure having the above-mentioned advantages is successfully provided through a relatively simple process of applying a centrifugal force to a viscous composition. The microstructure can be manufactured by the application of centrifugal force without a heat treatment.

Detailed description of each step of the method of the present invention is as follows;

Step (a): Preparing a Viscous Composition on a Lower Substrate

A substance used in the present invention to manufacture a microstructure is a viscous composition. In the present specification, a term "viscous composition" represents a composition, used in the present invention, whose shape is changed by a centrifugal force, thereby having an ability to form the microstructure.

Viscosity of the viscous composition may be controlled by an intrinsic viscosity of the viscous substance, and may be variously changed in accordance with a type, a concentration, or a temperature, etc. of a substance included in the composition to be suitable for aspects of the present invention. In addition, the viscosity may be controlled using an additional viscosity modifying agent in the viscous composition.

For example, a viscosity modifying agent commonly used in the related field, such as a hyaluronic acid and salt thereof, polyvinylpyrrolidone, cellulose polymer, dextran, gelatin, glycerin, polyethylene glycol, polysorbate, propylene glycol, povidone, carbomer, gum ghatti, guar gum, glucomannan, glucosamine, dammer resin, rennet casein, locust bean gum, microfibrillated cellulose, psyllium seed gum, xanthan gum, arabinogalactan, Arabic gum, alginic acid, gelatin, gellan gum, carrageenan, karaya gum, curdlan, chitosan, chitin, taragum, tamarind gum, tragacanth gum, furcelleran, pectin, or pullulan may be added to a composition including a main component of a microstructure, e.g. a biocompatible substance, thereby controlling the viscosity to be suitable for the present invention. Preferably, the viscous composition used in the present invention exhibits a viscosity equal to or less than 200,000 cSt.

According to an embodiment of the present invention, a viscous composition used in the present invention includes a biocompatible or a biodegradable substance. In the present specification, a term "biocompatible substance" represents a substance which is actually not toxic to a human body, is chemically inactive, and has no immunogenicity. In the present specification, a term "biodegradable substance" represents a substance that is degradable in vivo by a body fluid or a microorganism, etc.

Preferably, the viscous composition used in the present invention includes a hyaluronic acid and salt thereof, polyvinylpyrrolidone, cellulose polymer, dextran, gelatin, glycerin, polyethylene glycol, polysorbate, propylene glycol, povidone, carbomer, gum ghatti, guar gum, glucomannan, glucosamine, dammer resin, rennet casein, locust bean gum, microfibrillated cellulose, psyllium seed gum, xanthan gum, arabinogalactan, Arabic gum, alginic acid, gelatin, gellan gum, carrageenan, karaya gum, curdlan, chitosan, chitin, taragum, tamarind gum, tragacanth gum, furcelleran, pectin, or pullulan. More preferably, the viscous substance included in the viscous composition used in the present invention is a cellulose polymer, still more preferably is hydroxypropyl methylcellulose, a hydroxyalkyl cellulose (preferably, hydroxyethyl cellulose or hydroxypropyl cellulose), ethyl hydroxyethyl cellulose, alkyl cellulose, and carboxymethyl cellulose, even more preferably is hydroxypropyl methylcellulose or carboxymethyl cellulose, and most preferably is carboxymethyl cellulose.

Selectively, the viscous composition may include biocompatible and/or biodegradable substance as a main component.

A biocompatible and/or biodegradable substance that may be used in the present invention is, for example, polyester, polyhydroxyalkanoates (PHAs), poly($\alpha$-hydroxy acid), poly($\beta$-hydroxy acid), poly(3-hydroxybutyrate-co-valerate; PHBV), poly(3-hydroxyproprionate; PHP), poly(3-hydroxyhexanoate; PHH), poly(4-hydroxy acid), poly(4-hydroxybutyrate), poly(4-hydroxyvalerate), poly(4-hydroxyhexanoate), poly(esteramide), polycaprolactone, polylactide, polyglycolide, poly(lactide-co-glycolide; PLGA), polydioxanone, polyorthoester, polyetherester, polyanhydride, poly(glycolic acid-co-trimethylene carbonate), polyphosphoester, polyphosphoester urethane, poly(amino acid), polycyanoacrylate, poly(trimethylene carbonate), poly(iminocarbonate), poly(tyrosine carbonate), polycarbonate, poly(tyrosine arylate), polyalkylene oxalate, polyphosphagens, PHA-PEG (polyhydroxyalkanoate-polyethylene glycol), ethylene vinyl alcohol copolymer (EVOH), polyurethane, silicone, polyester, polyolefin, a copolymer of polyisobutylene and ethylene-$\alpha$-olefin, styrene-isobutylene-styrene triblock copolymer, acryl polymer and copolymer, vinyl halide polymer and copolymer, polyvinyl chloride, polyvinyl ether, polyvinyl methyl ether, polyvinylidene halide, polyvinylidene fluoride, polyvinylidene chloride, polyfluoroalkene, polyperfluoroalkene, polyacrylonitrile, polyvinyl ketone, polyvinyl aromatics, polystyrene, polyvinyl ester, polyvinyl acetate, ethylene-methyl metacrylate copolymer, acrylonitrile-styrene copolymer, ABS [poly(acrylonitrile, butadiene, styrene)] resin, ethylene-vinyl acetate copolymer, polyamide, alkid resin, polyoxymethylene, polyimide, polyether, polyacrylate, polymethacrylate, polyacrylic acid-co-maleic acid, chitosan, dextran, cellulose, heparin, hyaluronic acid, alginate, inulin, starch, or glycogen, and preferably is polyester, PHAs, poly($\alpha$-hydroxy acid), poly($\beta$-hydroxy acid), PHBV, PHP, PHH, poly(4-hydroxy acid), poly(4-hydroxybutyrate), poly(4-hydroxyvalerate), poly(4-hydroxyhexanoate), poly(esteramide), polycaprolactone, polylactide, polyglycolide, PLGA, polydioxanone, polyorthoester, polyetherester, polyanhydride, poly(glycolic acid-co-trimethylene carbonate), polyphosphoester, polyphosphoester urethane, poly(amino acid), polycyanoacrylate, poly(trimethylene carbonate), poly(iminocarbonate), poly(tyrosine carbonate), polycarbonate, poly(tyrosine arylate), polyalkylene oxalate, polyphosphagens, PHA-PEG, chitosan, dextran, cellulose, heparin, hyaluronic acid, alginate, inulin, starch, or glycogen.

According to a embodiment of the present invention, a viscous composition used in the present invention is dissolved in a proper solvent and exhibits viscosity. Meanwhile, among substances that exhibit viscosity, there are some substances that exhibit viscosity when melted by heat. To maximize an advantage of a non-heating process, which is one of the advantages of the present invention, a substance used in the viscous composition is one that exhibits viscosity when dissolved in the proper solvent.

A solvent which dissolves a viscous substance and is used in manufacturing the viscous composition is not particularly limited. Water, anhydrous or functional low-level alcohol of carbon numbers 1-4, acetone, ethyl acetate, chloroform, 1,3-buthylene glycol, hexane, diethyl ether, or butyl acetate may be used as the solvent. Preferably, the solvent is water or low-level alcohol, and most preferably, is water.

According to the embodiment of the present invention, the viscous composition further includes a drug. One main use of a microstructure of the present invention is a microneedle, and the microneedle aims at transdermal administration. Therefore, in a process of preparing the viscous composition, the drug is mixed with a biocompatible substance and prepared.

In the present specification, a term "microstructure" may be construed as a meaning that includes both a solid microstructure and a hollow microstructure.

The drug which may be used in the present invention is not particularly limited. For example, the drug includes a chemical drug, a protein drug, a peptide drug, nucleic acid molecules for gene therapy, and nanoparticles, etc.

The drug which may be used in the present invention includes, for example, an anti-inflammatory agent, an analgesic agent, an antiarthritic agent, an antispasmodic agent, an antidepressant, an antipsychotic agent, a nervous sedative, an antianxiety agent, a narcotic antagonist, an antiparkinsonism drug, a cholinergic agonist, an anticancer agent, an antiangiogenic agent, an immunosuppressant, an antiviral agent, an antibiotic agent, an anorexing agent, an analgesic agent, an anticholinergic agent, an antihistaminic agent, an anti-migraine agent, a hormone drug, a coronary, a cerebral, or a peripheral vasodilator, a contraceptive, an antithrombotic agent, a diuretic agent, an antihypertensive agent, a cardiovascular disorder therapeutic agent, a cosmetic component (e.g., an anti-wrinkle agent, a skin anti-aging agent, and a skin whitening agent), etc., but the drug is not limited thereto.

According to the embodiment of the present invention, a process for manufacturing a microstructure according to the present invention is practiced under a non-heating treatment. Therefore, even if the drug used in the present invention is a drug that is vulnerable to heat, such as a protein drug, a peptide drug, nucleic acid molecules for gene therapy, etc., manufacturing a microstructure including the drug is possible according to the present invention.

According to the embodiment of the present invention, a method of the present invention is used in manufacturing a microstructure which contains a heat-sensitive drug, more preferably a protein drug, a peptide drug, or a vitamin (preferably, vitamin C).

A protein/peptide drug which is contained in the microstructure by the method of the present invention is not particularly limited, and includes a hormone, a hormone analogue, an enzyme, an enzyme inhibitor, a signaling protein or a portion thereof, an antibody or a portion thereof, a single chain antibody, a binding protein or binding domain thereof, an antigen, an adhesion protein, a structural protein, a regulatory protein, a toxoprotein, a cytokine, a transcriptional regulatory factor, a blood coagulation factor, and a vaccine, etc., but is not limited thereto. In more detail, the protein/peptide drug includes insulin, an insulin-like growth factor 1(IGF-1), a growth hormone, erythropoietin, granulocyte-colony stimulating factors (G-CSFs), interferon alpha, interferon beta, interferon gamma, interleukin-1 alpha and beta, interleukin-3, interleukin-4, interleukin-6, interleukin-2, epidermal growth factors (EGFs), calcitonin, adrenocorticotropic hormone (ACTH), tumor necrosis factor (TNF), atobisban, buserelin, cetrorelix, deslorelin, desmopressin, dynorphin A (1-13), elcatonin, eleidosin, eptifibatide, growth hormone releasing hormone-11 (GHRH-11), gonadorelin, goserelin, histrelin, leuprorelin, lypressin, octreotide, oxytocin, pitressin, secretin, sincalide, terlipressin, thymopentin, thymosine al, triptorelin, bivalirudin, carbetocin, cyclosporine, exedine, lanreotide, luteinizing hormone-releasing hormone (LHRH), nafarelin, parathormone, pramlintide, T20 (enfuvirtide), thymalfasin, and ziconotide.

According to the embodiment of the present invention, the viscous composition further includes energy. In this case, the microstructure may be used to transmit or transfer energy forms such as thermal energy, light energy, and electrical energy. For example, in a photodynamic therapy, the microstructure may be used to induce light to a specific part in a body so the light may directly affect a tissue or the light affects a mediator such as a light-sensitive molecule.

A term "lower substrate" used to describe the method of the present invention corresponds to a term defined and used in the present specification to avoid confusion with terms "upper substrate" and "cover substrate" used in another aspect of the present invention. The lower substrate represents a substrate used for dropping or coating the viscous composition in step (a) of the method of the present invention. In the present specification, "lower substrate" may be generally understood as referring to a flat lower substrate, but the lower substrate does not always have to be flat, and may be of any shape as long as the lower substrate is able to form temporary mutual coupling with the viscous composition to prevent the viscous composition from being detached from the lower substrate as a centrifugal force is applied. Specifically, the lower substrate may be formed, for example, in a hollow cylindrical shape like an injection needle, and a cylindrical shape with a long aspect ratio like a needle (refer to FIG. 30).

The lower substrate for dropping or coating the viscous composition is not particularly limited, and may be manufactured with, for example, a substance such as a polymer, an organic chemical, a metal, a ceramic, and a semiconductor. When the viscous composition is dropped or coated on the lower substrate, the lower substrate itself may be used, or the lower substrate may be coated using a coating composition and used. In the present specification, a term "coating composition" is a composition used to coat the substrate used in the present invention, and represents a substance having viscosity being able to form various structures on the substrate. Although a different term has been used for the coating composition to be distinguished from the viscous composition which is dropped or coated on the lower substrate, types of substances which may be used are actually the same. Viscosity of the coating composition may be variously changed in accordance with a type, a concentration, a temperature of a substance included in the composition, an addition of a viscosity modifying agent, etc., and changed to be suitable for an aspect of the present invention.

In the present specification, a term "dropping" refers to preparing the viscous composition in a drop form on the substrate.

In the present specification, a term "coating" refers to forming a layer of a predetermined thickness of a particular substance on a target surface.

According to another embodiment of the present invention, a viscous composition is positioned on a lower substrate in a drop form. That is, the viscous composition may be dropped on the lower substrate in the drop form.

According to one detailed embodiment of the present invention, the drop changes properties of the viscous composition, properties of the lower substrate, or the properties of the viscous composition and the properties of the lower substrate, such that a shape and/or a contact area with the lower substrate of the drop is adjusted (FIG. 1).

The properties of the viscous composition are not particularly limited and may be any property as long as the property causes a change in the shape of the viscous composition when the viscous composition is dropped on the lower substrate, and are, for example, hydrophilicity and viscosity of the viscous composition. In addition, the properties of the lower substrate are not particularly limited and may be any property as long as the property causes a change in the shape of the viscous composition when the viscous composition is dropped on the lower substrate, and are, for example, hydrophilicity of the substrate, a roughness of a surface of the substrate, and a physical pattern or a hydrophilic pattern of the surface of the substrate. As a difference in hydrophilicity of the viscous composition and the lower substrate increases, a contact area between the viscous composition and the substrate becomes narrower, and a microstructure with a higher aspect ratio is formed when a centrifugal force is applied, when an equal amount of the viscous composition is dropped. Conversely, as the difference in the hydrophilicity of the viscous composition and the lower substrate decreases, the contact area between the viscous composition and the substrate becomes wider, and a microstructure with a lower aspect ratio is formed when the centrifugal force is applied. In addition, as a viscous composition with greater viscosity is used, a shape of a drop which is dropped on the lower substrate becomes closer to a spherical shape, and a microstructure with a higher aspect ratio is formed when the centrifugal force is applied. Conversely, as a viscous composition with smaller viscosity is used, a shape of a drop which is dropped on the lower substrate becomes closer to a widely spread shape, and a microstructure with a lower aspect ratio is formed when the centrifugal force is applied. Meanwhile, as the roughness of the surface of the lower substrate increases, a shape of a drop which is dropped on the substrate becomes closer to a spherical shape, and a microstructure with a higher aspect ratio is formed when the centrifugal force is applied. Conversely, as the roughness of the surface of the lower substrate decreases, a shape of a drop of the viscous composition which is dropped on the substrate becomes closer to a widely spread shape, and a microstructure with a lower aspect ratio is formed when the centrifugal force is applied.

A term "physical pattern of the surface of the substrate" which is used to describe the properties of the lower substrate refers to a pattern which is formed by cutting grooves in predetermined intervals on the substrate.

In addition, a term "hydrophilic pattern of the surface of the substrate" which is used to describe the properties of the lower substrate refers to a pattern in which hydrophilic regions and hydrophobic regions are repetitively arranged in predetermined intervals on the substrate.

Various applications of the physical pattern or the hydrophilic pattern of the surface of the substrate among the properties of the lower substrate are embodied as below:

According to a first detailed embodiment, a physical pattern is formed by cutting grooves in predetermined intervals on the lower substrate. In this case, as the viscous composition is coated or dropped on a physically-patterned region, the contact area between the viscous composition and the lower substrate may be narrowed, and when the centrifugal force is applied in step (b), a microstructure with a high aspect ratio may be formed. In this case, coating the viscous composition on an undesired region of the lower substrate is prevented, thus also minimizing loss of the viscous composition being used.

According to a second detailed embodiment, the lower substrate is designed such that hydrophilic regions and hydrophobic regions are repetitively arranged thereon. In this case, the viscous composition is coated or dropped on an easily adhered to region of the lower substrate in accordance with a hydrophilic or hydrophobic property of the viscous composition. For example, when the viscous composition is hydrophilic, the viscous composition is mostly coated or dropped on the hydrophilic regions of the lower substrate. In addition, the viscous composition may gather to the easily adhered to region of the lower substrate even when coated or dropped on the entirety of the lower substrate, such that the contact area between the viscous composition and the lower substrate may be narrowed, and a microstructure with a high aspect ratio may be formed when the centrifugal force is applied in step (b). As with the case of forming the physical pattern, coating the viscous composition on an undesired region of the lower substrate is also prevented in this case, thus minimizing loss of the viscous composition being used.

According to a third detailed embodiment, both of the first detailed embodiment and the second detailed embodiment are used. In this case, since grooves are physically formed on the lower substrate, the viscous composition may be prepared to be patterned. Also, the viscous composition is able to gather to a patterned region in accordance with an effect of gravity and chemical properties of the hydrophilic or hydrophobic viscous composition even when dropped on the entirety of the lower substrate, such that the contact area between the viscous composition and the lower substrate may be narrowed, and a microstructure with a high aspect ratio may be formed when the centrifugal force is applied in step (b).

According to another embodiment of the present invention, an amount of the viscous composition which forms the drop form may be adjusted to adjust a shape of the microstructure in various ways.

FIG. 2 illustrates a change in a shape of a microstructure which is formed by an application of centrifugal force in accordance with an amount of a viscous composition. When a predetermined or larger amount of the viscous composition is dropped in a drop form on the lower substrate, a microstructure with a spherical top portion is formed when the centrifugal force is applied.

Step (b): Applying Centrifugal Force to the Viscous Composition to Induce Extension of the Viscous Composition, Thereby Manufacturing a Microstructure Subsequently, a centrifugal force is applied to the viscous composition to induce an extension of the viscous composition, and the extended viscous composition is solidified, thereby manufacturing a microstructure having a high aspect ratio. FIG. 3 is a conceptual view of a method for manufacturing a microstructure using centrifugal force.

"applying a centrifugal force" in step (b) of the present invention refers to the lower substrate on which the viscous composition is dropped or coated moving in a circular motion to be in a state of receiving inertia in an opposite direction of an action of centripetal force.

The applying of the centrifugal force may be practiced through various methods well-known in the art. A device capable of fixing the lower substrate on which the viscous composition is prepared and rotating the lower substrate may be used, and preferably, a device in which a rotation speed, a rotation acceleration, and a rotation time are adjustable is used. The lower substrate on which the viscous composition is prepared is fixed to maintain a predetermined radial distance with a rotary axis and maintain a predetermined angle with a direction in which centrifugal force is applied in accordance with an extension direction of a desired microstructure, and the centrifugal force is applied.

A three-dimensional microstructure is formed through a process of solidifying the microstructure formed by the application of centrifugal force through rotation.

According to another embodiment of the present invention, step (b) may be practiced to enable the solidifying to occur at the same time. The viscous composition may be naturally solidified in a process of rotating the viscous composition.

According to another embodiment of the present invention, the present invention may adjust at least one dimension of the microstructure which is selected from the group formed of a length, a diameter, and an aspect ratio through adjusting the centrifugal force. A term "length" used in the present specification refers to a vertical length from a top portion of a microstructure to a surface of a support body. A term "top portion" of a microstructure which is used in the present specification refers to one end portion of a microstructure having a minimum diameter. A term "diameter" of a microstructure used in the present specification refers to a diameter of one end surface of a microstructure having a maximum value. In the present specification, "aspect ratio" signifies a ratio of length and diameter of a microstructure being formed. As the aspect ratio is increased, it signifies that the length is relatively longer and the diameter is relatively smaller. When the centrifugal force applied to the viscous composition increases, the diameter of the microstructure being formed becomes smaller, while the length and the aspect ratio thereof become larger. Conversely, when the centrifugal force being applied decreases, the diameter of the microstructure being formed becomes larger, while the length and the aspect ratio thereof becomes smaller (FIG. 4).

According to another embodiment of the present invention, the lower substrate of the present invention has a surface on which curves or embossed portions of a predetermined pattern is formed. Shapes of the curves or embossed portions are not particularly limited, and for example, as illustrated in FIG. 5, the lower substrate has a surface on which curves or embossed portions are formed. When the viscous composition is uniformly coated on the lower substrate having the surface on which the curves or embossed portions of the predetermined pattern are formed, and the centrifugal force is applied thereto, the viscous composition extends due to a phase difference of a high portion and a low portion on the substrate, thereby forming a microstructure.

According to one detailed embodiment of the present invention, the extension in step (b) of the present invention forms a top portion of the microstructure at a highest point of the curves or embossed portions in a direction of the centrifugal force. This is due to the phase difference of the high portion and the low portion on the substrate as mentioned above.

According to another embodiment of the present invention, the applying of the centrifugal force of the present invention is practiced with an adjusted rotational acceleration, thereby adjusting an extension angle of the viscous composition, thereby manufacturing a microstructure having a deformed shape. FIG. 6 illustrates a change in the shape of the microstructure in accordance with an adjusted rotational acceleration. As the rotational acceleration is maintained at a large value, the extension direction of the viscous composition is further bent toward an opposite direction of the rotation acceleration. By this, a microstructure of a deformed shape instead of a vertical shape may be obtained.

According to another embodiment of the present invention, the present invention provides a method which is capable of manufacturing a microstructure regardless of flatness or uniformity of the lower substrate (FIG. 7).

According to another embodiment of the present invention, the present invention provides a method which further includes a step (ab) between the steps (a) and (b): (ab) covering the viscous composition prepared on the lower substrate with a cover substrate having holes.

Shapes of the holes are not particularly limited, and may be variously selected in accordance with a desired shape of a microstructure. For example, the holes are formed in a circular, an oval, or a polygonal shape (FIG. 8*a*). As illustrated in FIG. 8*b*, when the centrifugal force is applied after the viscous composition prepared on the lower substrate is covered with the cover substrate having holes, the viscous composition at positions of the holes of the cover substrate passes through the holes of the cover substrate, thereby inducing extension of the viscous composition and forming a microstructure. A term "cover substrate" used to describe the present embodiment corresponds to a term defined and used in the present specification to be distinguished from the term "lower substrate" used in the other embodiments and a term "upper substrate" to be used. Preparing the cover substrate is the same as the description of the lower substrate, and description of overlapping parts will be omitted to avoid excessive complexity of description of the present specification.

According to another embodiment of the present invention, step (b) of the present invention is practiced using an additional upper substrate, the upper substrate is positioned at an upper portion which is spatially apart from the viscous composition, the extension of the viscous composition in step (b) enables a portion of the viscous composition to be coupled to the upper substrate, whereby a method for manufacturing a microstructure in which two microstructures are connected to each other between the lower substrate and the upper substrate or respectively coupled to the lower substrate and the upper substrate and separated from each other is provided.

The term "upper substrate" used to describe the present embodiment corresponds to a term defined and used in the present specification to be distinguished from the terms "lower substrate" and "cover substrate" used in the other embodiments. Preparing the upper substrate is the same as the description of the lower substrate, and description of overlapping parts will be omitted to avoid excessive complexity of the description of the present specification. FIG. 9 illustrates a conceptual view of the present embodiment.

The viscous composition prepared on the lower substrate extends by the centrifugal force applied thereto, and comes in contact with and is coupled to the upper substrate. Here, a microstructure, which is formed by two microstructures connected to each other between the lower substrate and the upper substrate or respectively coupled to the lower substrate and the upper substrate and separated from each other, is manufactured. In the present embodiment, a distance between the lower substrate and the upper substrate may be adjusted to adjust a shape of a microstructure being formed (FIG. 10). As illustrated in FIG. 10, as the distance between the two substrates becomes longer, a thinner and longer microstructure with a higher aspect ratio is obtained. In addition, in the present embodiment, the shape of the microstructure being formed may be variously changed in accordance with an amount of time in which the centrifugal force is applied (FIG. 11). As the amount of time in which the centrifugal force is applied becomes longer, an amount of the viscous composition attached to the upper substrate increases. In addition, in the present embodiment, a magnitude of the centrifugal force being applied may be adjusted to variously change the shape of the microstructure being formed (FIG. 12). As the magnitude of the centrifugal force being applied becomes larger, an amount of the viscous composition attached to the upper substrate increases. In addition, in the present embodiment, an amount of the viscous composition dropped in a drop form on the substrate may be adjusted to variously change the shape of the microstructure being formed (FIG. 13). As the amount of the viscous composition becomes greater, the magnitude of the centrifugal force acting on the viscous composition becomes larger, causing the amount of the viscous composition attached to the upper substrate to increase.

According to another embodiment of the present invention, the microstructure is a microstructure formed by two microstructures connected to each other between the lower substrate and the upper substrate, and the present invention provides a method which further includes the following step (c) after the step (b): (c) moving at least one of the lower substrate and the upper substrate to cut the microstructure formed by two microstructures connected to each other.

According to one detailed embodiment of the present invention, the cutting is performed by moving at least one of the lower substrate and the upper substrate in a certain direction, and by this, a tip having a particular angle is formed at the microstructure.

A term "tip" used to describe the present invention refers to a tip portion of the top portion of the microstructure. That is, the "tip" signifies an end portion of the microstructure which is the farthest from a surface at which the viscous composition is coming in contact with the lower substrate. When the cutting in the step (c) is performed by moving at least one of the lower substrate and the upper substrate in the certain direction, the tip is made to have a bevel angle (FIG. 14). The bevel angle formed at the tip of the microstructure is described in Korean Patent No. 1195974, and content of the patent may be used as a reference to describe the bevel angle of the present specification. In the step (c), the bevel angle may be simply adjusted through setting a direction of the moving at least one of the lower substrate and the upper substrate.

According to another embodiment of the present invention, in the embodiment using the additional upper substrate, the viscous composition may be a hydrophilic substance, and at least one surface of the lower substrate and the upper substrate may have a hydrophobic property. In addition, conversely, the viscous composition may be a hydrophobic substance, and at least one surface of the lower substrate and the upper substrate may have a hydrophilic property.

Like this, when hydrophilic properties of the viscous composition and at least one surface of the lower substrate and the upper substrate are different, the microstructure may be formed as illustrated in FIG. 15 or FIG. 16.

According to an aspect of the present invention, the present invention provides a method for manufacturing a microstructure including the following steps (reference: upper row in FIG. 29):

(a) preparing a viscous composition on an inner space of a hollow structure including a viscous composition discharge unit; and (b) applying a centrifugal force to the viscous composition to enable the viscous composition to be discharged through the discharge unit of the hollow structure to induce an extension of the viscous composition, thereby manufacturing a microstructure.

With respect to another aspect of the present invention mentioned above, an aspect of the present invention has a characteristic of using the hollow structure including the viscous composition discharge unit instead of the lower substrate. "Hollow structure including a viscous composition discharge unit" in the present specification may be one substrate including one or more openings as the viscous composition discharge unit, and may use a cylindrical hollow structure (reference: FIG. 29).

According to one detailed embodiment of the present invention, a "hollow structure" of the present invention is a cylindrical hollow structure. In more detail, for example, a cylindrical cylinder having a shape of an injection needle may be used. The viscous composition is positioned in an empty space, which is an inner opening of the hollow structure, the centrifugal force is applied, and the viscous composition is discharged to the outside from the opening of the hollow structure through the viscous composition discharge unit by the centrifugal force and extends, thereby forming a microstructure. A term "viscous composition discharge unit" in the present specification refers to a portion in which the inner empty space of the hollow structure is exposed to the outside of the hollow structure, and a passage between the inner space and the outside of the hollow structure. In terms of the cylindrical hollow structure, the "viscous composition discharge unit" refers to an end of an opening in the cylindrical structure which receives the greatest centrifugal force. Since an aspect of the present invention has a characteristic of using the hollow structure including the viscous composition discharge unit instead of the lower substrate with respect to the method for manufacturing a microstructure using the lower substrate mentioned above, overlapping parts will be omitted to avoid excessive complexity of the description of the present specification.

As an application of the method for manufacturing a microstructure of the present invention, an upper substrate on which a microstructure is already formed (reference: upper substrate in FIG. 25) may be used to manufacture a multi-layer microstructure (reference: FIG. 26). The "multi-layer microstructure" in the present specification refers to a microstructure which is formed of two or more layers formed through a repetition of the process for manufacturing a microstructure (reference: (A) in FIG. 25), or includes another microstructure inside the microstructure (reference: (B) in FIG. 25).

As another application of the method for manufacturing a microstructure of the present invention, with respect to the method for manufacturing a microstructure using the lower substrate and the upper substrate, positions of the lower substrate on which a microstructure is formed and the upper substrate may be changed with each other, the process for manufacturing a microstructure may be additionally performed, and, by this, microstructures of a plurality of shapes may be fabricated on one flat surface (reference: FIG. 27). Through a repetition of the same manufacturing process, microstructures of various shapes may be fabricated on one flat surface.

According to another aspect of the present invention, the present invention provides a microstructure manufactured by the methods.

Microstructures are utilized in various fields due to their physical properties and advantages such as a high degree of accumulation. The microstructures may be utilized as various uses such as a microneedle for maximizing efficiency of drug delivery, a micro electro mechanic system (MEMS) based on photolithography, and a semiconductor element.

According to still another aspect of the present invention, as illustrated in FIG. 17, the present invention provides a device for manufacturing a microstructure by centrifugal force including the followings: (a) a rotary arm 2 connected to a rotary shaft of a centrifuge; and (b) a lower substrate 1 connected to the rotary arm and accommodating a viscous composition.

The rotary arm may be integrally provided with the rotary shaft of the centrifuge, or provided in a form which is coupled to and separated from the rotary shaft. The rotary arm may be provided in a length-adjustable form, a radius of rotation of the viscous composition is determined by the length of the rotary arm, and this acts as a factor for determining a magnitude of the centrifugal force. The lower substrate may be integrally provided with the rotary arm, or provided in a form which is attached to and separated from the rotary arm. Accommodating the viscous composition in the lower substrate refers to the viscous composition being dropped or coated on the lower substrate.

According to an embodiment of the present invention, the device for manufacturing a microstructure by centrifugal force, which is the present invention, further includes a rotary shaft 3 (FIG. 18)

According to another detailed embodiment of the present invention, the device further includes a motor 4 which provides rotary force to the rotary shaft 3 of the centrifuge (FIG. 18).

According to another detailed embodiment of the present invention, the device may further include a housing which surrounds an outer portion of the above configuration. By this, safety of the device may be ensured, and an external obstacle that may interfere when a microstructure is being manufactured may be blocked.

According to an aspect of the present invention, the present invention provides a method for manufacturing a hollow microstructure including the following steps (reference: lower row of FIG. 29):

(a) depositing a metal on a microstructure manufactured in accordance with another aspect of the present invention mentioned above;

(b) metal-plating the metal-deposited microstructure;

(c) removing the microstructure to obtain a hollow microstructure.

In an aspect of the present invention, the microstructure manufactured in accordance with another aspect of the present invention mentioned above acts as a mold for manufacturing the hollow microstructure. The metal deposition in the step (a) of the present invention corresponds to a process for enabling a metal plating reaction for manufacturing a subsequent hollow microstructure to occur better.

In the present specification, a term "deposition" refers to vaporizing or sublimating a substance to be coated with a physical method or chemical method to improve a mechanical strength of the substance and allowing the substance to coagulate on a surface of a substrate in atomic or molecular units, thereby forming a film. As the deposition of the present invention, all physical vapor deposition and chemical vapor deposition commonly used in the art may be used. A deposited metal of the present invention is, for example, stainless steel, aluminum (Al), chrome (Cr), nickel (Ni), gold (Au), silver (Ag), copper (Cu), titanium (Ti), cobalt (Co), or alloys thereof. In a more detailed example, Tollens reaction may be used to chemically deposit silver (Ag).

As in the step (b) of the present invention, the hollow microstructure may be manufactured by plating a pre-manufactured microstructure. According to the present invention, a plating thickness may be adjusted to adjust various external elements, i.e. outer diameter and hardness, of a finally manufactured hollow microneedle. As the plating thickness increases, the outer diameter and the hardness of the hollow microneedle increase. A plating material used in the present invention includes, for example, nickel, stainless steel, aluminum, chrome, a cobalt base alloy, titanium, and alloys thereof, but is not limited thereto. Any bioapplicable metal known in the art that has no toxicity or carcinogenicity, is not rejected by a human body, has fine mechanical properties such as tensile strength, modulus of elasticity, wear resistance etc., and has corrosion resistance capable of withstanding a corrosive environment in the human body may be used as the plating material. In a detailed example, the plating metal is aluminum (Al), chrome (Cr), nickel (Ni), gold (Au), silver (Ag), copper (Cu), titanium (Ti), cobalt (Co), or alloys thereof.

After the plating, an inner microstructure formed of the viscous composition may be removed to form the hollow microstructure formed of plated metal. The inner microstructure formed of the viscous composition may be dissolved using a proper organic solvent, burned, or physically removed. The process for manufacturing a hollow microstructure may further include a process of cutting a top portion of the microstructure to form an opening at the tip portion of the microstructure.

According to an aspect of the present invention, the present invention provides a method for manufacturing a drug sealed type microstructure which includes the following steps:

(a) preparing a viscous composition on an inner space of a hollow structure including a viscous composition discharge unit; and (b) applying a centrifugal force to the viscous composition to enable the viscous composition to be discharged through the discharge unit of the hollow structure to induce an extension of the viscous composition, thereby manufacturing a microstructure; and (c) injecting a drug into the microstructure through the discharge unit while the centrifugal force is being applied in the step (b) or after the applying of the centrifugal force is finished.

A term "drug sealed type microstructure" in the present specification refers to a microstructure in which an additional drug is included in a sealed form in a solid structure. In the manufacturing of the microstructure of the above-mentioned another aspect of the present invention, the viscous composition may be a substance having a pharmaceutical effect itself or include a substance having the pharmaceutical effect, but an additional drug may be further included in the microstructure as in an aspect of the present invention. The drug is not particularly limited and may preferably include a drug that is suitable to being provided through subject's skin. A detailed example of the drug is given in another aspect of the present invention.

According to an aspect of the present invention, the present invention provides a method for manufacturing a hollow microstructure which includes the following steps:

(a) preparing a viscous composition on an inner space of a hollow structure including a viscous composition discharge unit;

(b) applying a centrifugal force to the viscous composition to enable the viscous composition to be discharged through the discharge unit of the hollow structure to induce an extension of the viscous composition, thereby manufacturing a microstructure; and (c) injecting a gas or fluid into a solid microstructure through the discharge unit while the centrifugal force is being applied in the step (b) or after the applying of the centrifugal force is finished to form an empty space (reference: FIG. 31).

With respect to the above-mentioned another aspect of the present invention related to the method for manufacturing a hollow microstructure through metal plating, an aspect of the present invention corresponds to a method which is capable of providing the hollow microstructure formed of the viscous composition without using the processes of metal deposition, plating, and removing the solid microstructure. The method for manufacturing a hollow microstructure, which is the present invention, is practiced by the same method with the above-mentioned method for manufacturing the "hollow structure including the viscous composition discharge unit", but further includes forming an empty space by injecting a gas or a fluid in the solid microstructure through the discharge unit while the centrifugal force is being applied or after the applying of the centrifugal force is finished. The hollow microstructure may be manufactured through a process of injecting a gas or a fluid in the solid microstructure, and a process of removing the gas or the fluid may be additionally included as needed. In addition, according to whether an opening is formed at the top portion of the formed microstructure, cutting the top portion of the microstructure may be further included.

Advantageous Effects

Characteristics and advantages of the present invention may be summarized as follows:

(a) The present invention provides a method capable of manufacturing a solid microstructure even without performing a heat treatment. By this, various substances that are sensitive to heat and easily destroyed or deformed can be mounted in the microstructure. This further expands an applicable field of a microneedle.

(b) According to the present invention, a microstructure may be fabricated in a contactless way without coming in contact with another structure such as a mold or a pillar which were used in the prior art. This enables to overcome a loss and a limitation in fabrication yield that used to occur due to a separation process or a cutting process through physical destruction from a structure that was in contact after formation of the microstructure is completed.

(c) The present invention provides a method for manufacturing a microstructure at a high yield regardless of flatness or uniformity of a substrate.

(d) The present invention provides a method for manufacturing microstructures of various shapes through adjusting an amount of dropped viscous composition, properties of the viscous composition and the substrate, a radius of rotation, a rotational acceleration, a rotational speed, a rotational duration time etc.

(e) The present invention enables a microstructure having a designed shape and dimension (e.g. a diameter or an aspect ratio) by a relatively rapid and simple process. This characteristic enables the microstructure to be mass-produced and a quality of the microstructure to be well-managed.

(f) In the present invention, in case of a method using a lower substrate and an upper substrate, more microstructures can be produced by a single process.

DESCRIPTION OF DRAWINGS

FIG. 1 illustrates microstructures formed when a centrifugal force is applied after dropping drops of a viscous composition on a lower substrate in different shapes and contact areas.

FIG. 2 illustrates microstructures formed when the centrifugal force is applied after dropping different amounts of the viscous composition on the lower substrate.

FIG. 3 illustrates a conceptual view of a method for applying the centrifugal force on the lower substrate on which the viscous composition is prepared.

FIG. 4 illustrates microstructures formed when different magnitudes of the centrifugal force are applied.

FIG. 5 illustrates microstructures formed when the viscous composition is coated on the lower substrate including curves or embossed portions of a specific pattern and the centrifugal force is applied.

FIG. 6 illustrates microstructures formed when different rotational acceleration values are applied.

FIG. 7 illustrates microstructures being formed by an application of the centrifugal force regardless of flatness and uniformity of the lower substrate.

FIG. 8a illustrates a plan view of a cover substrate.

FIG. 8b illustrates an embodiment in which the cover substrate is used.

FIG. 9 illustrates an embodiment which further includes an upper substrate.

FIG. 10 illustrates shapes of microstructures formed when a distance between the upper substrate and the lower substrate is varied.

FIG. 11 illustrates shapes of microstructures formed on the upper substrate and the lower substrate in accordance with an amount of time of applying the centrifugal force, according to the embodiment which further includes the upper substrate.

FIG. 12 illustrates shapes of microstructures formed on the upper substrate and the lower substrate in accordance with a magnitude of the centrifugal force being applied, according to the embodiment which further includes the upper substrate.

FIG. 13 illustrates shapes of microstructures formed on the upper substrate and the lower substrate in accordance with an amount of dropped viscous composition, according to the embodiment which further includes the upper substrate.

FIG. 14 illustrates a bevel angle formed when at least one of the lower substrate and the upper substrate is moved and microstructures formed by being connected to each other are cut, according to the embodiment which further includes the upper substrate.

FIG. 15 illustrates microstructures which are formed when one of the upper substrate and the lower substrate is hydrophobic when a hydrophilic viscous composition is used, according to the embodiment which further includes the upper substrate.

FIG. 16 illustrates microstructures which are formed when one of the upper substrate and the lower substrate is hydrophilic when a hydrophobic viscous composition is used, according to the embodiment which further includes the upper substrate.

FIG. 17 illustrates a device for manufacturing a microstructure by centrifugal force.

FIG. 18 illustrates the device for manufacturing a microstructure by centrifugal force which further includes a rotary shaft of a centrifuge and a motor.

FIG. 19 illustrates a shape of a microstructure formed by applying the centrifugal force.

FIG. 20 illustrates microstructures manufactured through the applying of the centrifugal force using the lower substrate and the upper substrate.

FIG. 21 illustrates a result of observing the microstructures manufactured through the applying of the centrifugal force using the lower substrate and the upper substrate with an electron microscope.

FIG. 22 illustrates a solid microstructure manufactured on the lower substrate and a dissolved state of the microstructure four hours after the microstructure is applied to skin, with respect to the manufacturing of the microstructure through the applying of the centrifugal force and using the lower substrate and the upper substrate.

FIG. 23 illustrates a microstructure manufactured on the upper substrate and a dissolved state of the microstructure four hours after the microstructure is applied to skin, with respect to the manufacturing of the microstructure through the applying of the centrifugal force and using the lower substrate and the upper substrate.

FIG. 24 illustrates a result of observing a shape of a microstructure manufactured while changing the magnitude of the centrifugal force being applied.

FIG. 25 is a mimetic view of a method for manufacturing a microstructure which (A) has multi-layers or (B) includes another microstructure inside using the upper substrate on which a microstructure is already formed.

FIG. 26 illustrates a multi-layer microstructure having a plurality of layers manufactured using the upper substrate on which a microstructure is already formed.

FIG. 27 illustrates a method for manufacturing microstructures of a plurality of shapes which further performs the process of manufacturing the microstructure by changing positions of the lower substrate on which the microstructure is formed and the upper substrate, with respect to the method for manufacturing a microstructure using the lower substrate and the upper substrate.

FIG. 28 illustrates the microstructures of a plurality of shapes which are manufactured by the method of further performing the process of manufacturing the microstructure by changing positions of the lower substrate on which the microstructure is formed and the upper substrate, with respect to the method for manufacturing a microstructure using the lower substrate and the upper substrate.

FIG. 29 illustrates a mimetic view of a method for manufacturing a microstructure using a hollow structure, which includes a viscous composition discharge unit, instead of the lower substrate, and a method for manufacturing a hollow microstructure through a process of plating the microstructure formed by the above method.

FIG. 30 illustrates a method for forming a microstructure using a lower substrate in a form of a needle instead of dropping or coating the viscous composition on the flat lower substrate.

FIG. 31 illustrates a process of forming a hollow microneedle by simultaneously forming a microstructure using centrifugal force and injecting a gas or fluid through the viscous composition discharge unit and forming an empty space in a microneedle.

EMBODIMENTS

Hereinafter, the present invention will be described in more detail through embodiments. The embodiments are only for describing the present invention in more detail, and it will be apparent to those of ordinary skill in the art that the scope of the present invention is not limited by the embodiments in accordance with the present invention.

EMBODIMENTS

Embodiment 1: Manufacture of Microstructure with High Aspect Ratio Using Centrifugal Force After coating carboxymethylcellulose (Sigma-Aldrich, Inc.) to a polystyrene substrate (SPL Life Science), a viscous solution drop of 40 wt % hyaluronic acid (Soliance) was formed. Then, the substrate was mounted on a centrifuge (Beckman coulter), the centrifuge was accelerated at 5 g/s, and was operated for three minutes at a gravitational acceleration of 900 g. Then, the centrifuge was decelerated at a velocity of 9 g/s. Through the centrifugal force application process, a microstructure with a high aspect ratio was manufactured (reference: FIG. 19) having an effective length of 1,500 μm, a top portion diameter of 45 μm, and a bottom portion diameter of 300 μm.

Meanwhile, a separate process of solidifying the manufactured microstructure was not required, and the solidifying simultaneously occurred in the process of applying the centrifugal force.

Consequently, it can be realized that the microstructure of a high aspect ratio can be successfully fabricated through the centrifugal force application process of the present invention.

Embodiment 2: Manufacture of Microstructure Using Two Substrates (Inner and Outer Substrates)

After discharging 40% (w/v) of 29 kDa hyaluronic acid solution on an aluminum substrate, which is a lower substrate, for 0.220 seconds at a pressure of 0.200 MPa using a dispenser (MUSASHI engineering, ML-5000XII) and forming a solution drop, a centrifuge (Hanil science industrial, Combi 514R) was used to rotate the solution drop between two aluminum substrates, which are respectively the lower substrate and an upper substrate, spaced apart by 1 mm, by a centrifugal force of 500 g for 30 seconds, thereby forming a microstructure (reference: FIG. 20). A left-side figure of FIG. 20 is a microstructure formed on the lower substrate (inner substrate), and a right-side figure of FIG. 20 is a microstructure formed on the upper substrate (outer substrate).

Embodiment 3: Check Microstructure Formation Through Electron Microscope

The microstructure that was manufactured by Embodiment 2 was observed with an electron microscope (Field Emission Scanning Electron Microscope, JSM-7001F, JEOL Ltd., Japan). The microstructures were formed on both the upper substrate and the lower substrate (reference: FIG. 21).

Embodiment 4: Human Body Absorption Evaluation of Microstructure Patch

After applying a microstructure patch manufactured by Embodiment 2 to human body skin, whether the microstructure was absorbed was checked after four hours. FIG. 22 is a result of using the microstructure formed on the lower substrate in Embodiment 2, and FIG. 23 is a result of using the microstructure formed on the upper substrate in Embodiment 2. In both cases, it was confirmed that the microstructures were dissolved and absorbed into the human body.

Embodiment 5: Aspect Ratio Change Test of Microstructure in Accordance with Change in Centrifugal Force With respect to the manufacturing of the microstructure by the method of Embodiment 2, only the lower substrate was used without the upper substrate, and a shape of a microstructure being formed was observed after applying a centrifugal force of 400 g or 500 g. It was confirmed that the aspect ratio of the formed microstructure was higher in a case of applying the centrifugal force of 500 g than in a case of applying the centrifugal force of 400 g (reference: FIG. 24), and this shows that the shape of the microstructure being formed can be adjusted by adjusting the magnitude of the centrifugal force being applied.

Embodiment 6: Manufacture of Multi-Layer Microstructure

With respect to the method for manufacturing a microstructure of Embodiment 2 in which the lower substrate and the upper substrate are used, the upper substrate on which a microstructure is already formed (reference: upper substrate in FIG. 25) was used to manufacture a microstructure. A multi-layer microstructure was manufactured by a new microstructure being layered on the microstructure that was already formed on the upper substrate (reference: FIG. 26). This shows that the method for manufacturing a microstructure using centrifugal force can be easily applied in manufacturing microstructures of various shapes or manufacturing microstructures formed of a plurality of substances.

Embodiment 7: Manufacture of Microstructures of Plurality of Shapes

With respect to the method for manufacturing a microstructure of Embodiment 2 in which the lower substrate and the upper substrate are used, positions of the lower substrate on which a microstructure is formed and the upper substrate were changed with each other, and the process of manufacturing a microstructure of Embodiment 2 was additionally performed (reference: FIG. 27). By this process, microstructures of two shapes were fabricated on one flat surface (reference: FIG. 28). This shows that microstructures of various shapes can be fabricated on one flat surface through repetition of the manufacture process.

Hereinbefore, particular parts of the present invention have been described in detail. It should be apparent to those of ordinary skill in the art that the detailed description is only a embodiment, and the scope of the present invention is not limited by the description. Consequently, the substantial scope of the present invention should be construed as being defined by the attached claims and their equivalents.

The invention claimed is:

1. A method for manufacturing a microstructure, the method comprising:
   applying a viscous material onto a surface of a substrate; and
   rotating the substrate about an axis such that the surface faces away from the axis while rotating, which causes the viscous material to extend generally in a direction perpendicular to the surface and away from the axis by centrifugal force applied to the viscous material, thereby providing a microstructure comprising at least one microneedle elongated from and attached to the surface,
   wherein the method adjusts at least one dimension of the microstructure which is selected from the group consisting of a length, a diameter, and an aspect ratio by adjusting the centrifugal force.

2. The method according to claim 1, wherein the viscous material comprises at least one selected from the group consisting of a biocompatible substance, a biodegradable substance and a drug.

3. The method according to claim 1, wherein applying the viscous material comprises forming at least one drop of the viscous material on the surface.

4. The method according to claim 1, wherein the surface is curved or embossed to provide hills and valleys.

5. The method according to claim 4, wherein the at least one microneedle comprises a plurality of microneedles, wherein the viscous material is applied onto the surface such that the viscous material forms a layer that generally follows contour of the hills and valleys of the surface, wherein rotating the substrate causes the viscous material to extend from areas over the hills of the surface such that at least part of the resulting microneedles are elongated from and attached to the hills of the surface.

6. The method according to claim 1, wherein the substrate is substantially flat.

7. The method according to claim 1, further comprising:
   providing a device comprising a body and a plurality of through-holes that are extending from a first surface of the body to a second surface of the body; and after applying the viscous material and before rotating the substrate, placing the device on the viscous material such that the viscous material contacts the first surface;
   wherein rotating the substrate causes the viscous material extend into at least part of the plurality of through-holes.

8. The method according to claim 1, wherein the substrate is referred to as a first substrate, wherein the surface of the first substrate is referred to as a first surface wherein the method further comprises:
   arranging a second substrate with a second surface such that the second surface opposes and faces the first surface when rotating the first substrate,
   wherein rotating the first substrate causes the viscous material to extend such that one end of the viscous material contacts and is attached to the second surface while the other end of the viscous material is attached to the first surface.

9. The method according to claim 8, wherein the viscous material is a hydrophilic substance, the first surface is hydrophobic and the second surface is hydrophilic, wherein the method further comprising:
   moving the second substrate away from the first substrate in the direction, which causes the viscous material is detached from the first surface while the viscous material is attached to the second surface.

10. The method according to claim 8, further comprising moving the second substrate relative to the first substrate in the direction or in another direction perpendicular to the direction, which causes the viscous material to be separated at an intermediate point between the two ends of the viscous material to provide another microstructure.

11. The method according to claim 1, further comprising:
    depositing a first metal layer over the microstructure to provide a metal-deposited microstructure;
    plating a second metal layer onto the first metal layer of the metal-deposited microstructure to provide a metal-plated microstructure; and
    removing hardened viscous material from the metal-plated microstructure to obtain a micro-mold comprising the first metal layer and the second metal layer.

12. A method for manufacturing a microstructure, the method comprising:
    providing a hollow structure comprising an inner space and an outlet, the hollow structure containing a viscous material within the inner space; and
    rotating the hollow structure about an axis, which causes at least a portion of the viscous material to move out through the outlet and extend away from the outlet by centrifugal force applied to the viscous material, thereby providing a microstructure comprising a microneedle elongated from and attached to the hollow structure,
    wherein the method adjusts at least one dimension of the microstructure which is selected from the group consisting of a length, a diameter, and an aspect ratio by adjusting the centrifugal force.

13. The method of claim 12, wherein the hollow structure comprises a piston and further contains another material, wherein the method further comprises:
    moving the piston to inject the other material into the microstructure while the centrifugal force is applied or after the centrifugal force is applied, wherein the other material comprises a drug, gas or fluid.

* * * * *